US009687541B2

(12) United States Patent
Middaugh et al.

(10) Patent No.: US 9,687,541 B2
(45) Date of Patent: Jun. 27, 2017

(54) **PHARMACEUTICAL COMPOSITIONS CONTAINING *CLOSTRIDIUM DIFFICILE* TOXOIDS A AND B**

(71) Applicant: Sanofi Pasteur Biologics, LLC, Cambridge, MA (US)

(72) Inventors: C. Russell Middaugh, Lawrence, KS (US); Richard Fahrner, Boxford, MA (US); Peter Ciarametaro, Gloucester, MA (US)

(73) Assignee: Sanofi Pastuer Biologies, LLC, Cambridge, MA (US)

( * ) Notice: Subject to any disclaimer, the term of this patent is extended or adjusted under 35 U.S.C. 154(b) by 0 days.

(21) Appl. No.: 15/083,428

(22) Filed: Mar. 29, 2016

(65) Prior Publication Data

US 2016/0317640 A1 Nov. 3, 2016

Related U.S. Application Data

(62) Division of application No. 12/677,864, filed as application No. PCT/US2008/010767 on Sep. 15, 2008, now Pat. No. 9,320,790.

(60) Provisional application No. 60/972,496, filed on Sep. 14, 2007.

(51) Int. Cl.

| | |
|---|---|
| ***A61K 39/08*** | (2006.01) |
| ***A61K 9/00*** | (2006.01) |
| ***A61K 9/19*** | (2006.01) |
| ***A61K 47/08*** | (2006.01) |
| ***A61K 47/12*** | (2006.01) |
| ***A61K 47/26*** | (2006.01) |
| *A61K 39/00* | (2006.01) |

(52) U.S. Cl.

CPC ............ *A61K 39/08* (2013.01); *A61K 9/0019* (2013.01); *A61K 9/19* (2013.01); *A61K 47/08* (2013.01); *A61K 47/12* (2013.01); *A61K 47/26* (2013.01); *A61K 39/00* (2013.01); *A61K 2039/55505* (2013.01)

(58) Field of Classification Search

None

See application file for complete search history.

(56) References Cited

U.S. PATENT DOCUMENTS

| | | | |
|---|---|---|---|
| 4,879,218 | A | 11/1989 | Wilkins et al. |
| 5,624,914 | A | 4/1997 | Patel et al. |
| 5,736,139 | A | 4/1998 | Kink et al. |
| 5,902,565 | A | 5/1999 | Cox et al. |
| 6,214,341 | B1 | 4/2001 | Thomas, Jr. et al. |
| 6,544,518 | B1 | 4/2003 | Friede et al. |
| 6,599,715 | B1 | 7/2003 | Vanderberg et al. |
| 6,969,520 | B2 | 11/2005 | Thomas, Jr. et al. |
| 9,320,790 | B2 | 4/2016 | Middaugh et al. |
| 2004/0235139 | A1 | 11/2004 | Demain et al. |
| 2006/0099227 | A1 | 5/2006 | Hunt |
| 2007/0134199 | A1 | 6/2007 | Frevert |
| 2011/0045025 | A1 | 2/2011 | Middaugh et al. |

FOREIGN PATENT DOCUMENTS

| | | | |
|---|---|---|---|
| CA | 2474943 | A1 | 8/2003 |
| EP | 0438747 | A1 | 7/1991 |
| EP | 0754463 | A2 | 1/1997 |
| EP | 0892054 | A1 | 1/1999 |
| EP | 1568378 | A1 | 8/2005 |
| EP | 1686137 | A1 | 8/2006 |
| JP | H03-193735 | A | 8/1991 |
| JP | H08-333277 | A | 12/1996 |
| JP | H11-510793 | A | 9/1999 |
| JP | 2006-528137 | A | 12/2006 |
| JP | 2007-514749 | A | 6/2007 |
| RU | 2011126602 | A | 1/2013 |
| WO | WO-96/11699 | A1 | 4/1996 |
| WO | WO-97/02835 | A1 | 1/1997 |
| WO | WO-99/20304 | A1 | 4/1999 |
| WO | WO-03/068260 | A1 | 8/2003 |
| WO | WO-03/088946 | A1 | 10/2003 |
| WO | WO-2005/035573 | A1 | 4/2005 |
| WO | WO-2006/020208 | A2 | 2/2006 |
| WO | WO-2006/044577 | A1 | 4/2006 |
| WO | WO-2006/079722 | A2 | 8/2006 |
| WO | WO-2007/044809 | A2 | 4/2007 |
| WO | WO-2008/057550 | A2 | 5/2008 |
| WO | WO-2010/063693 | A1 | 6/2010 |

OTHER PUBLICATIONS

Decision of Rejection for Japanese Patent Application No. 2013-241821, dated Jun. 29, 2016 (6 pages).

Decision on Grant a Patent for the Invention for RU 2010114730/10, dated Aug. 19, 2014 (16 pages).

English language translation of PCT Publication No. WO 2006/079722-A2, published Aug. 3, 2006 (16 pages).

English language translation of PCT Publication No. WO 2006/079722-A2, published Aug. 3, 2006 (32 pages).

Extended European Search Report for EP08830210.4, mailed Feb. 7, 2012.

Goodnough et al. "Stabilization of Botulinum Toxin Type A During Lyophilization," Applied and Enviro. Microbio. 58: 3426-3428 (1992).

International Preliminary Report on Patentability for International Application No. PCT/US2008/010767, mailed Mar. 25, 2010.

International Search Report for International Application No. PCT/US2008/010767, mailed Dec. 3, 2008.

Notice of Reasons for Rejection for Japanese Application No. 2013-241821, mailed Nov. 11, 2015 (7 pages).

Office Action for Chinese Patent Application No. CN 200880116603.0, issued Jul. 3, 2012.

(Continued)

*Primary Examiner* — Brian J Gangle

(74) *Attorney, Agent, or Firm* — Clark & Elbing LLP; Susan M. Michaud

(57) ABSTRACT

This invention relates to compositions including *Clostridium difficile* toxins and/or toxoids and corresponding methods. The compositions of the invention include one or more excipients that increase stability and/or decrease aggregation of the toxins.

32 Claims, 18 Drawing Sheets

(56) References Cited

OTHER PUBLICATIONS

Passot et al. "Physical characterisation of formulations for the development of two stable freeze-dried proteins during both dried and liquid storage" Eur J Pharm Biopharm.. 60(3):335-48 (2005).
Wang, "Instability, stabilization, and formulation of liquid protein pharmaceuticals," In J Pharm. 185(2):129-88 (1999).
Written Opinion for International Application No. PCT/US2008/010767, mailed Dec. 3, 2008.
Carpenter et al., "Rational design of stable lyophilized protein formulations: theory and practice," Rational Design of Stable Protein Formulations, New York. p. 109, 112-33 (2002) (23 pages).
Extended European Search Report for European Patent Application No. 16174817.3, dated Dec. 21, 2016, Middaugh et al., "Pharmaceutical Compositions Containing Clostridium Difficile Toxoids A and B," filed Sep. 15, 2008 (9 pages).

Toxoid A , CD (secondary structure)

- Secondary structure does not change with pH except for pH 5.5
- Secondary structure is complex, where the helical structure dominates.

Toxoid B , CD (secondary structure)

- Secondary structure does not change with pH
- Secondary structure is complex, where the helical structure dominates.

PHARMACEUTICAL COMPOSITIONS CONTAINING *CLOSTRIDIUM DIFFICILE* TOXOIDS A AND B

FIELD OF THE INVENTION

This invention relates to compositions including *Clostridium difficile* toxoids and corresponding methods.

BACKGROUND OF THE INVENTION

*Clostridium difficile* (*C. difficile*) toxins A and B are responsible for *C. difficile*-associated disease (CDAD), which manifests itself as nosocomial diarrhea and pseudomembranous colitis (Kuijper et al., Clinical Microbiology and Infection 12(Suppl. 6):2-18, 2006; Drudy et al., International Journal of Infectious Diseases 11(1):5-10, 2007; Warny et al., Lancet 366(9491):1079-1084, 2005; Dove et al., Infection and Immunity 58(2):480-488, 1990; Barroso et al., Nucleic Acids Research 18(13):4004, 1990). Treatment of the toxins with formaldehyde results in the corresponding toxoids A and B, which are completely inactivated and retain at least partial immunogenicity (Torres et al., Infection and Immunity 63(12):4619-4627, 1995). It has been shown that vaccination employing both toxoids is effective in hamsters, healthy adults, and patients with recurrent CDAD (Torres et al., Infection and Immunity 63(12):4619-4627, 1995; Kotloff et al., Infection and Immunity 69(2):988-995, 2001; Sougioultzis et al., Gastroenterology 128(3):764-770, 2005; Torres et al., Vaccine Research 5(3):149-162, 1996). Additionally, the administration of both free and aluminum salt (adjuvant) bound toxoids leads to appropriate immune responses (Torres et al., Vaccine Research 5(3):149-162, 1996; Giannasca et al., Infection and Immunity 67(2):527-538, 1999). The administration of both toxoids simultaneously is more effective than administration of the individual proteins alone (Kim et al., Infection and Immunity 55(12):2984-2992, 1987). Both the A and B toxoids are thus candidates for vaccine development. Improvement of their conformational integrity and/or reduction in their tendency to aggregate is desirable to produce optimal storage stability.

SUMMARY OF THE INVENTION

The invention provides compositions, such as pharmaceutical compositions (e.g., vaccine compositions), including a toxin or a toxoid of *Clostridium difficile* (e.g., a toxoid of *C. difficile* toxins A and/or B; with toxoids A and B being present in a ratio of, for example, 5:1 to 1:5, e.g., 3:2 (A:B)) and one or more pharmaceutically acceptable excipients, which reduce or delay aggregation of the toxin and/or toxoid, and/or increase thermal stability of the toxin or toxoid, relative to a composition lacking the one or more pharmaceutically acceptable excipients. In one example, the one or more pharmaceutically acceptable excipients reduces or delays aggregation of the toxin and/or toxoid by 50% or more, relative to a composition lacking the one or more pharmaceutically acceptable excipients. In another example, the one or more pharmaceutically acceptable excipients increases the thermal stability of the toxin and/or toxoid by 0.5° C. or more, relative to a composition lacking the one or more pharmaceutically acceptable excipients. Optionally, the compositions of the invention can include an adjuvant (e.g., an aluminum compound, such as an aluminum hydroxide, aluminum phosphate, or aluminum hydroxyphosphate compound). The compositions can be in liquid form, dry powder form, freeze dried, spray dried, or foam dried.

The one or more pharmaceutically acceptable excipients can be, for example, selected from the group consisting buffers, tonicity agents, simple carbohydrates, sugars, carbohydrate polymers, amino acids, oligopeptides, polyamino acids, polyhydric alcohols and ethers thereof, detergents, lipids, surfactants, antioxidants, salts, human serum albumin, gelatins, formaldehyde, or combinations thereof. In various examples, (i) the buffer is selected from the group consisting of citrate, phosphate, glycine, histidine, carbonate, and bicarbonate, and is at a concentration of 5-100 mM; (ii) the tonicity agent is mannitol, at a concentration of 1-50 mM; (iii) the sugar is selected from sorbitol, trehalose, and sucrose, at a concentration of 1-30%; (iv) the amino acid, oligopeptide, or polyamino acid is present at a concentration of up to 100 mM; (v) the polyhydric alcohol is selected from the group consisting of glycerol, polyethylene glycol, and ethers thereof of molecular weight 200-10,000, at a concentration of up to 20%; (vi) the detergents and lipids are selected from the group consisting of sodium deoxycholate, TWEEN 20 (polysorbate 20), TWEEN 80 (polysorbate 80), and PLURONICS (polyoxamer block copolymers), at concentrations of up to 0.5%; (vii) the carbohydrate polymers are selected from dextran and cellulose; (viii) the salts are selected from the group consisting of sodium chloride, potassium chloride, magnesium chloride, and magnesium acetate, up to 150 mM; and (ix) the formaldehyde is present at 0.001-0.02%.

Specific examples of such excipients include those listed in Table 1, Table 2, Table 8, or Table 9. In other examples, the compositions include comprises sodium or potassium citrate, and/or sodium or potassium phosphate, optionally in combination with sucrose and/or formaldehyde. Thus, in various examples, the compositions include *Clostridium difficile* toxoids A and B, 5-100 mM (e.g., 10-30 mM, or 20 mM) sodium or potassium citrate (or phosphate), 2-20% (e.g., 2-10% or 5%) sucrose, and ≤0.020% (e.g., 0.016%) formaldehyde, pH 5.5-8.5 (e.g., 6.5-8.0, or 7.5). In other examples, a combination of sorbitol, dextrose, and/or TWEEN 80 is used.

The invention also provides methods of making compositions including a toxin or a toxoid of *Clostridium difficile* and one or more pharmaceutically acceptable excipients, which reduce or delay aggregation of the toxin and/or toxoid, and/or increase thermal stability of the toxin or toxoid, relative to a composition lacking the one or more pharmaceutically acceptable excipients. These methods include providing a toxin or a toxoid of *Clostridium difficile* and admixing the toxin or toxoid of *Clostridium difficile* with the one or more pharmaceutically acceptable excipients, such as those described herein. The compositions may be stored in liquid form or lyophilized, as described herein.

The invention further provides methods of inducing an immune response to *C. difficile* in a subject, which involve administering to the subject a composition as described herein. In one example, the patient does not have, but is at risk of developing, *C. difficile* disease, and in another example, the patient has *C. difficile* disease. In addition, the invention includes use of the compositions of the invention in inducing an immune response to *C. difficile* in a subject, or in preparation of medicaments for use in this purpose.

The invention provides several advantages. For example, use of the excipients described herein can result in increased physical stability of *C. difficile* toxoids A and B, and/or decreased or delayed aggregation, which are important for the production of pharmaceutical products (e.g., vaccines)

including the toxoids. Further, use of the ratios of the invention (e.g., 3:2, A:B) and adding adjuvant just prior to administration (rather than in formulation of stored vaccine), can lead to increased immunogenicity.

Other features and advantages of the invention will be apparent from the following detailed description, the drawings, and the claims.

DETAILED DESCRIPTION

Figure 1A:
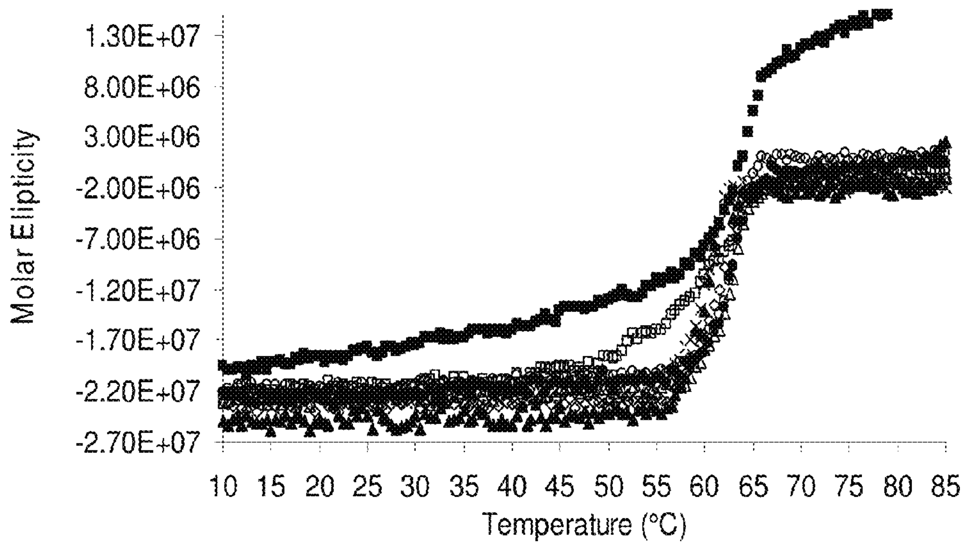
FIG. 1. Studies of solute effects on the structural stability of toxoid A (x) in presence of 20% trehalose (□), 20% sucrose (■), 10% sorbitol (○), 10% dextrose (●), 20% glycerol (Δ), 0.05% TWEEN 80 (▲), 0.1% PLURONIC F68 (nonionic polyoxyethylene-polyoxypropylene block co-polymer) (◇): (a) CD signal at 208 nm; (c) ANS emission intensity; (d) ANS emission peak position; and (b) DSC thermogram. The thermal traces represent an average of 2 measurements, where each data point had a standard error of less than 0.5.
Figure 1B:
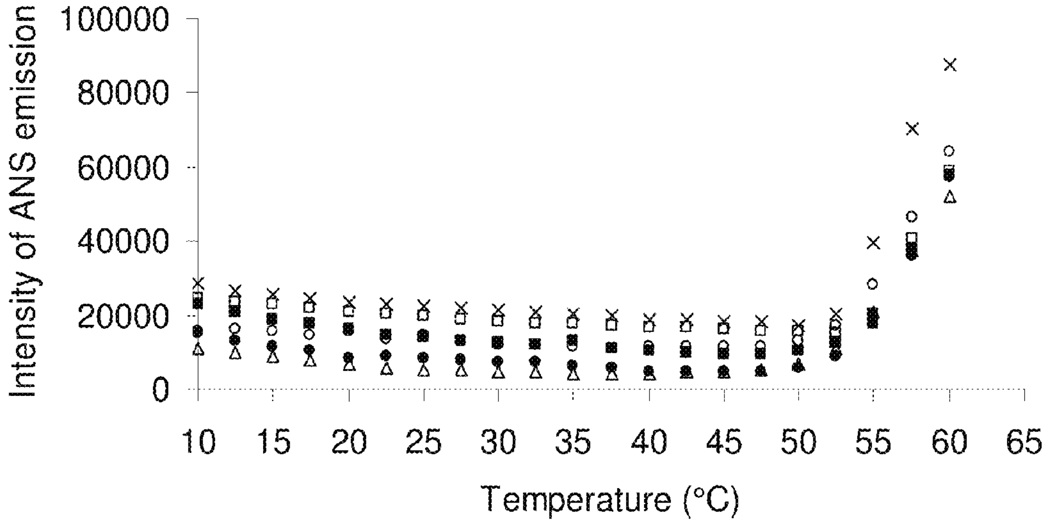
Figure 1C:
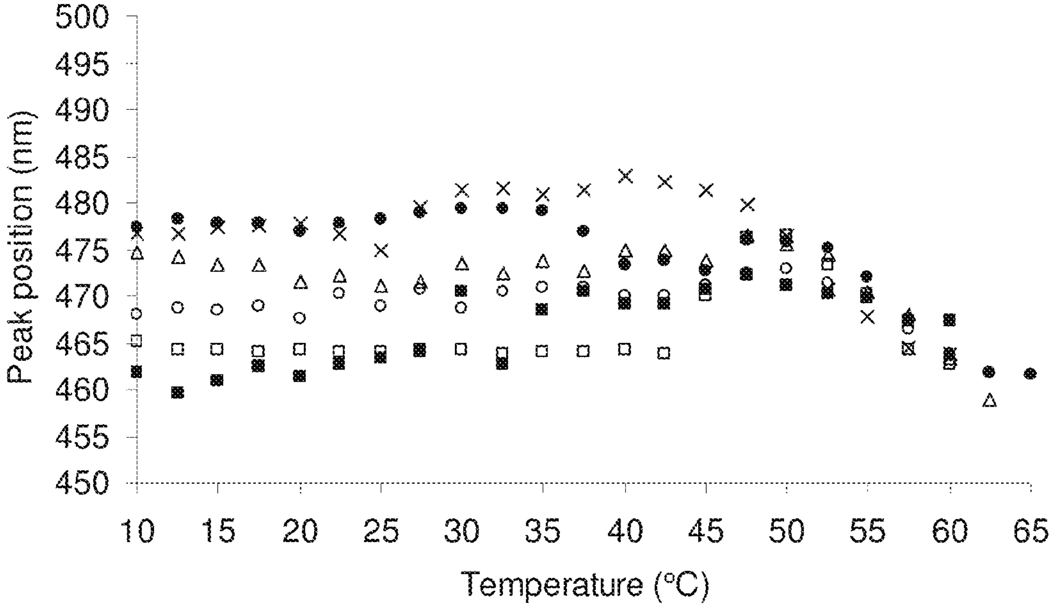
Figure 1D:
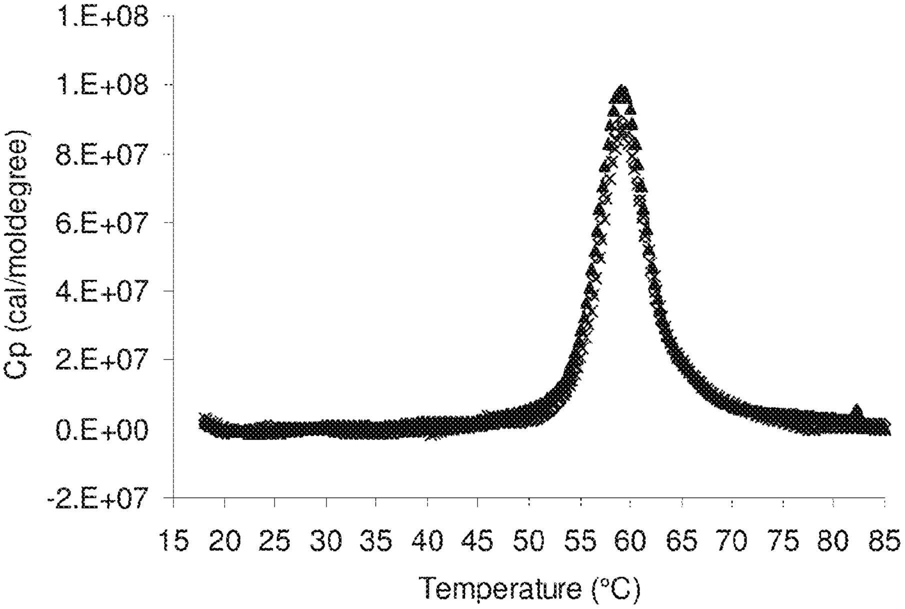
Figure 2A:
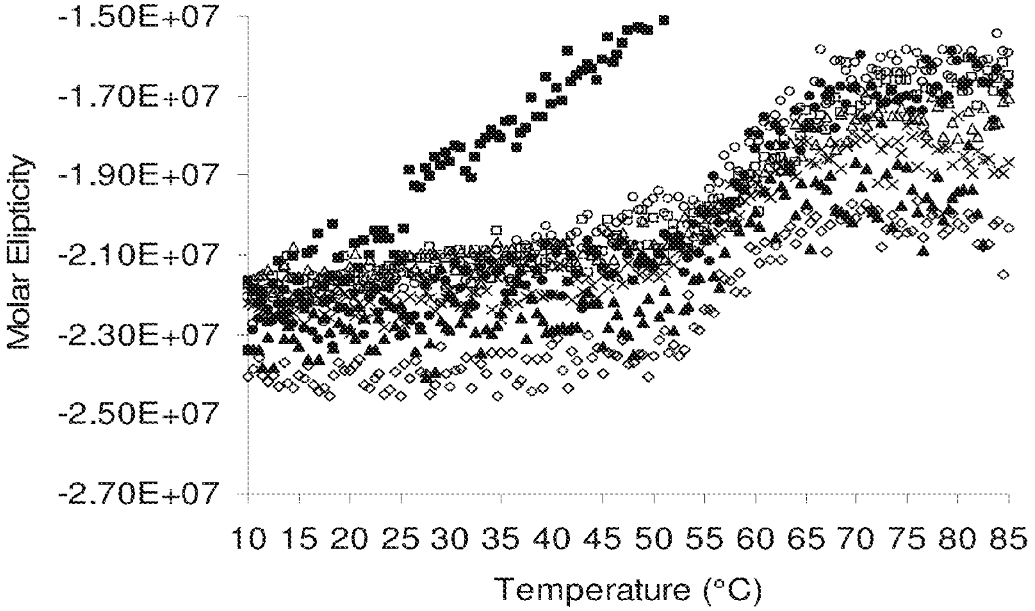
FIG. 2. Studies of solute effects on the structural stability of toxoid B (x) in presence of 20% trehalose (□), 20% sucrose (■), 10% sorbitol (○), 10% dextrose (●), 20% glycerol (Δ), 0.05% TWEEN 80 (▲), 0.1% PLURONIC F68 pluronic F68. (◇): (a) CD signal at 208 nm; (c) ANS emission intensity; (d) ANS emission peak position; and (b) DSC thermograms. The thermal traces represent an average of 2 measurements. Each data point had a standard error of less than 0.5.
Figure 2B:
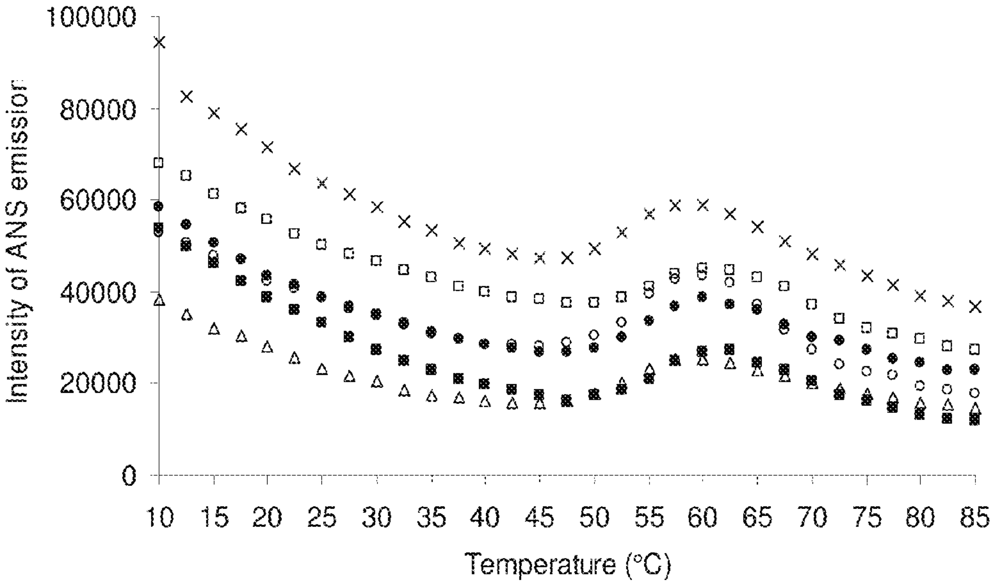
Figure 2C:
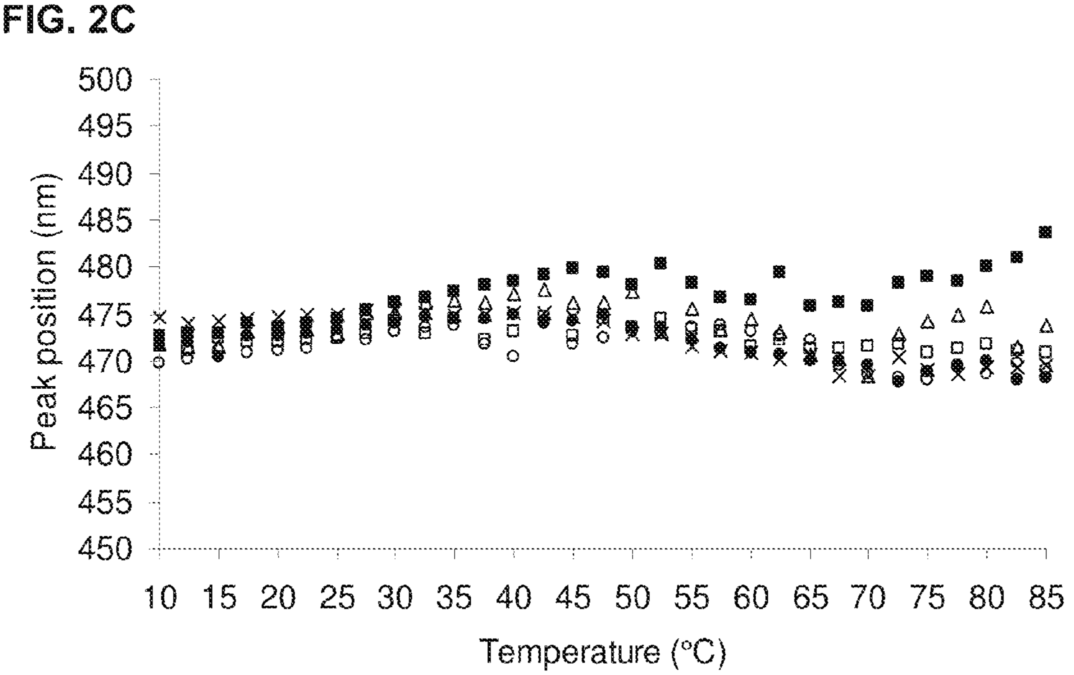
Figure 2D:
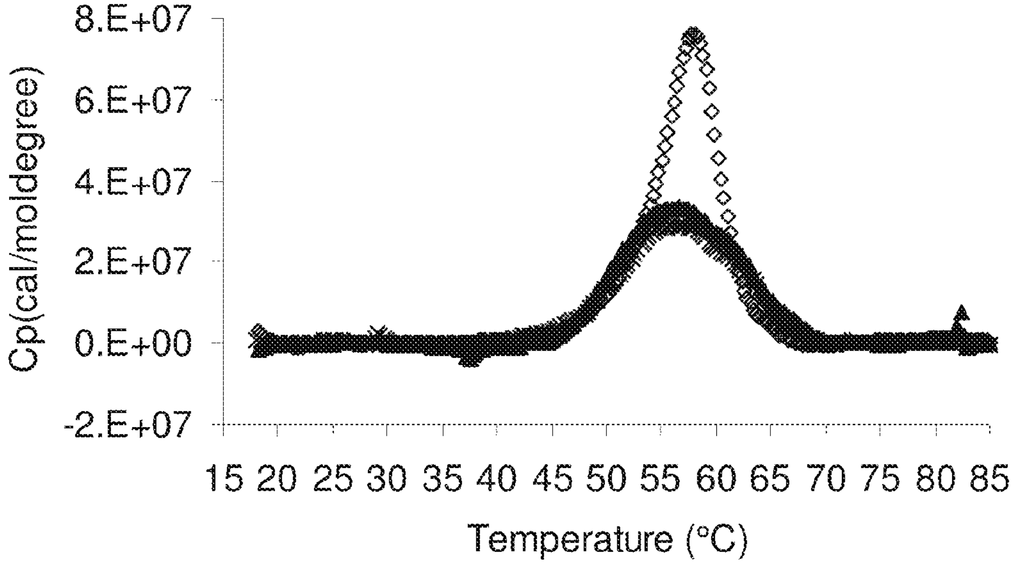

The invention provides compositions including *Clostridium difficile* toxins and/or toxoids and one or more pharmaceutically acceptable excipients that provide beneficial properties to the compositions. For example, and as described further below, excipients included in compositions of the invention can result in increased stability of one or more of the toxoid components of the compositions and/or decreased or delayed aggregation of the toxoids.

*C. difficile* toxoids that can be included in the compositions of the invention can be made using any of a number of methods known in the art. For example, methods involving inactivation with formaldehyde can be used (see, e.g., Kotloff et al., Infection and Immunity 69(2):988-995, 2001). Preferably, the compositions include both toxoid A and toxoid B, but compositions including only one of these toxoids are also included in the invention. An exemplary *C. difficile* strain that can be used as a source of toxins is ATCC 43255 (VPI 10463). The toxoids can be present in the compositions in varying ratios, e.g., 5:1 (A:B) to 1:5 (A:B). In specific examples, the ratios may be 2:1, 3:1, or 3:2 (A:B). The total amount of toxoid in the compositions of the invention can be, e.g., 100 ng-1 mg, 100 ng-500 μg, 1-250 μg, 10-100 μg, 25-75 μg, or 50 μg. The compositions may optionally be stored in vials in single unit dosage.

The compositions of the invention include one or more compounds such as, for example, buffers (e.g., citrate, phosphate, glycine, histidine, carbonate, or bicarbonate; 5-100 mM; examples of citrates salts that can be used include sodium, potassium, magnesium and zinc); tonicity agents (e.g., mannitol; 1-50 mM); carbohydrates, such as sugars or sugar alcohols (e.g., sorbitol, trehalose, or sucrose;

1-30%) or carbohydrate polymers (e.g., dextran and cellulose); amino acids, oligopeptides, or polyamino acids (up to 100 mM); polyhydric alcohols (e.g., glycerol, polyethylene glycols, or ethers thereof, of molecular weight 200-10,000, and concentrations of up to 20%); detergents, lipids, or surfactants (e.g., TWEEN 20, TWEEN 80, or PLURONICS, with concentrations up to 0.5%); antioxidants; salts (e.g., sodium chloride, potassium chloride, magnesium chloride, or magnesium acetate, up to 150 mM); albumin (e.g., human serum albumin); gelatins; formaldehyde (0.001-0.02%); or combinations thereof.

Examples of excipients that can be used in the compositions of the invention include those that are listed in Tables 1, 2, 8, and 9, below. In various examples, the excipients may be those that result in (i) increased thermal stability (e.g., of at least 0.5° C., e.g., 0.5-5° C., 1-4° C., or 2-3° C.) as measured by, e.g., the assays described below (e.g., Differential Scanning calorimetry (DSC)), and/or (ii) decreased or delayed aggregation of toxoid A, toxoid B, or both toxoids A and B of, for example, 50% or more (e.g., 60% or more, 70% or more, 80% or more, 90% or more, 95% or more, 98% or more, 99% or more, or 100%), as measured, for example, by assays described below. Compositions including toxoid aggregates are also included in the invention.

Exemplary excipients and buffers thus include sodium citrate (e.g., 0.01-0.2 M, e.g., 0.02-0.1 M), sucrose (e.g., 1-20% or 5-10%), sorbitol (e.g., 4-20% or 5-10%), trehalose (e.g., 4-20% or 5-10%), TWEEN 80 (e.g., 0.05-0.1%), diethanolamine (e.g., 0.3 M), histidine (e.g., 0.02-0.3 M), guanidine (e.g., 0.3 M), dextrose (e.g., 5-20%), glycerol (e.g., 20%), albumin (e.g., 1-2.5%), lactose (e.g., 10-20%), mannitol (e.g., 10%), sucrose (e.g., 5-20%), PLURONIC F-68 (e.g., 0.1%), 2-OH propyl β-CD (e.g., 5-10%), dextran T40 (e.g., 0.03-0.08 mg/ml), BRIJ (Polyoxyethyleneglycol dodecyl ether) (e.g., 0.01-0.1%), lysine (e.g., 0.3 M), Tween 20 (e.g., 0.01-0.05%), and aspartic acid (e.g., 0.15 M)(see Tables 1, 2, 8, and 9). These excipients can be used in the invention in the concentrations listed in the tables. Alternatively, the amounts can be varied by, e.g., 0.1-10 fold, as is understood in the art. Other carbohydrates, sugar alcohols, surfactants, and amino acids that are known in the art can also be included in the compositions of the invention.

The excipients and buffers can be used individually or in combination. As an example of a combination, the compositions can include sodium citrate and sucrose, which has been shown to provide benefits with respect to toxoid stability. The amounts of these components can be, for example, 10-30 mM, 15-25 mM, or 20 mM sodium citrate; and 1-20% or 5-10% sucrose. In addition to these components, such compositions may include a low amount of formaldehyde, such as 0.001-0.020, 0.01-0.018, or 0.16% formaldehyde. The pH of such a composition can be, e.g., 5.5-8.0 or 6.5-7.5, and the composition can be stored at, e.g., 2-8° C., in liquid or lyophilized form. In variations of this composition, the sodium citrate may be replaced with sodium phosphate (10-30 mM, 15-25 mM, or 20 mM) and/or the sucrose can be replaced with sorbitol (e.g., 4-20% or 5-10%), or trehalose (e.g., 4-20% or 5-10%). Other variations of the compositions are included in the invention, and involve use of other components listed herein. Based on the above, an exemplary composition of the invention includes 20 mM sodium citrate, 5% sucrose, and 0.016% formaldehyde, pH 7.5.

In another example, the compositions include sorbitol, dextrose, and TWEEN 80, which is a combination that has been shown to provide benefits with respect to aggregation and stability (see below). The amounts of these components can be, for example, 5-15%, 8-12%, or 10% sorbitol; 5-15%, 8-12%, or 10% dextrose; and 0.01-1%, 0.025-0.5%, or 0.05-0.1% TWEEN 80. A specific example in which these components are present at 10% (sorbitol and dextrose) and 0.05-0.1% TWEEN 80) is described below. In another example, the excipients are dextrose (10%) and sorbitol (10%).

The compositions of the invention can be stored in liquid or dried form, with the latter including as examples lyophilized powder form, freeze dried form, spray dried form, and foam dried form. Thus, in addition to one or more excipient, as described above, the compositions of the invention can include a liquid medium (e.g., saline or water), which may be buffered with, e.g., sodium phosphate (e.g., 5 mM) containing NaCl (e.g., 150 mM). An exemplary pH range of the compositions of the invention is 5-10, e.g., 5-9, 5-8, 5.5-9, 6-7.5, or 6.5-7. Further, the compositions can include one or more stabilizing agents. In other examples, the compositions are in lyophilized form, and such compositions may be reconstituted by use of a liquid medium (e.g., saline or water) prior to administration.

The compositions of the invention can optionally include one or more adjuvants, in addition to the toxoid or toxin antigens and the excipient(s) described above. Adjuvants that can be used in the invention include aluminum compounds, such as aluminum hydroxide, aluminum phosphate, and aluminum hydroxy phosphate. The antigen can be precipitated with, or adsorbed onto, the aluminum compound using standard methods. As a specific example, alum (e.g., REHYDRAGEL LV® Reheis, Inc., Berkeley Heights, N.J.; up to, e.g., 2 mg AlOH/dose, e.g., about 1.5 mg AlOH/dose; ALHYDROGEL® (e.g., ALHYDROGEL® 2%; (aluminum hydroxide adjuvant)), Brenntag Biosectror, Frederickssund, Denmark ($AlOH_3$)) can be used. The amount of aluminum used can be, for example, 100-850 μg/dose, 200-600 μg/dose, or 300-600 μg/dose.

One approach to formulation included in the invention involves formulating the toxoids and excipients together, and then adding an adjuvant, such as an alum adjuvant, just prior to administration. This approach has been found to increase immunogenicity, as described further below. In another approach, the adjuvant is included in the formulation prior to storage (either in liquid or lyophilized form). Additional adjuvants that can be used in the compositions and methods of the invention include RIBI (ImmunoChem, Hamilton, Mont.), QS21 (Aquila), Bay (Bayer), and Polyphosphazene (Virus Research Institute, Cambridge, Mass.; WO 95/2415).

The invention also includes methods of making the compositions described herein, which involve production of toxoids as described, e.g., by Kotloff et al., Infection and Immunity 69(2):988-995, 2001, and combining the toxoids with one or more excipient as described herein using standard methods of pharmaceutical formulation. As described above, the compositions can be stored in liquid or lyophilized form. Lyophilization can be carried out using standard methods (see, e.g., the examples below), and lyophilized material may be reconstituted in a sterile liquid (e.g., water, saline, or a solution including any desired excipient(s)), with or without an adjuvant, prior to administration.

Further, the invention includes use of the compositions in the prevention and treatment of *C. difficile* infection or disease. Thus, the invention includes administration of the compositions of the invention to prevent or treat *C. difficile* associated disease (CDAD), such as recurrent CDAD, as well as features of CDAD including diarrhea (e.g., nosocomial diarrhea) and pseudomembranous colitis. As is known in the art, CDAD is often associated with treatment of subjects with antibiotics, such as subjects who are hospitalized. Thus, the treatment methods of the invention can be used in treatment of such patients. In addition, treatment according to the invention can be combined with antibiotic (e.g., vancomycin and/or metronidazole) treatment and/or passive immunotherapy (see, e.g., U.S. Pat. No. 6,214,341). The administration methods of the invention can also be used in the generation of *C. difficile* immunoglobulin for use in passive immunization of patients (see, e.g., U.S. Pat. No. 6,214,341).

The invention also includes methods of identifying excipients that can be used to generate compositions including *C. difficile* toxins or toxoids having improved properties. These methods involve screening assays, such as those described further below, which facilitate the identification of conditions resulting in decreased or delayed aggregation and/or increased stability of one or more of the toxin and/or toxoid components of the compositions. These methods include aggregation assays and stability assays as described further below. Further, the invention includes the use of other assays for identifying desirable formulations, including solubility, immunogenicity, and viscosity assays.

The compositions of the invention can be administered by, for example, the percutaneous (e.g., intramuscular, intravenous, or intraperitoneal) route in amounts and in regimens determined to be appropriate by those skilled in the art. For example, 100 ng-1 mg, 100 ng-500 μg, 1-250 μg, 10-100 μg, 25-75 μg, or 50 μg toxoid can be administered. For the purposes of prophylaxis or therapy, the vaccine can be administered, for example, 1, 2, 3, or 4 times. When multiple doses are administered, the doses can be separated from one another by, for example, one week to a month. In another example, four doses of 50 μg each can be administered intramuscularly over any eight-week period.

Example I

To identify conditions that enhance the physical stability of *Clostridium difficile* toxoids A and B, screening for stabilizing compounds was performed. The screening of 30 GRAS (generally regarded as safe) compounds at various concentrations and in several combinations was performed in two parts. First, a high-throughput aggregation assay was used to screen for compounds that delay or prevent aggregation of toxoids under stress conditions (toxoids at pH 5-5.5 were incubated at 55° C. for 55 or 75 minutes). Compounds that stabilized both proteins were further studied for their ability to delay unfolding under conditions leading to a presumably native-like folded state (pH 6.5). The thermal stability of the toxoids on the surface of ALHYDROGEL® (aluminum hydroxide adjuvant) was monitored with DSC and also showed significant improvement in the presence of certain excipients. Compounds that effectively inhibited aggregation of both toxoids were further investigated for their ability to enhance the structural stability of the proteins. To identify stabilizing agents for adjuvant-bound toxoids, selected excipients were further studied for their ability to enhance the thermal stability of adjuvant-bound toxoids. In conclusion, this study has generated information concerning the behavior of free and adjuvant-bound toxoids under a range of conditions (temperatures and solutes) that can be used to design pharmaceutical formulations of enhanced physical stability.

Experimental Materials and Methods

Materials

Toxoids A and B were produced in highly purified form using methods described previously (Kotloff et al., Infection and Immunity 69(2):988-995, 2001). The concentration of the proteins was determined by UV absorbance at 280 nm using absorbance units of 1.173 for toxoid A and 0.967 for toxoid B at concentrations of 1 mg/mL, respectively. All reagents used were of analytical grade and were purchased from Sigma (St. Louis, Mo.). Sodium phosphate buffer (5 mM, pH 5.0, 5.5, and 6.5) containing 150 mM NaCl was used for the excipient screening studies. Sodium phosphate buffer (5 mM, pH 6.5) containing 150 mM NaCl was used for the agitation and adjuvant studies. For buffer exchange, protein was dialyzed at refrigerator temperature using SLIDE-A-LYZER® Dialysis Cassettes, 10 kDa MWCO (Pierce, Rockford, Ill.).

Excipient Screening Studies

Aggregation Assay.

Approximately 30 GRAS (generally regarded as safe) compounds in 58 variations of concentration and in several combinations were screened for their abilities to inhibit the aggregation of the toxoids. Aggregation of the protein was monitored by optical density measurements at 350 nm (OD 350 nm) using a 96-well plate reader (Spectra Max M5, Molecular Devices, Sunnyvale, Calif.). The aggregation assay was performed at pH 5.5 for toxoid A (1.2 mg/ml) and at pH 5.0 for toxoid B (0.5 mg/ml) at 55° C. Under these conditions, the proteins are partially unfolded and spontaneously associate. Thus, any stabilizing influence of the excipients that perturbs these two processes can be potentially detected. The protein was added to the wells of a 96-well plate containing excipient(s) at the corresponding pH and the samples were incubated at 55° C. for 75 minutes in the case of toxoid A and 55 minutes for toxoid B. The optical density of the solutions was monitored at 350 nm every 5 minutes. Controls of protein solutions without added compounds and buffer alone with excipient(s) (blanks) were examined simultaneously. The measurements were corrected for intrinsic buffer-excipient behavior by subtracting the blanks prior to data analysis. Each sample was evaluated in triplicate. Percent inhibition of aggregation was calculated employing the following expression:

$$\%\text{ inhibition of aggregation} = 100 - \left[\frac{\Delta OD_{350}(E)}{\Delta OD_{350}(C)} \times 100\right]$$

Where $\Delta OD_{350}$ (E) represents the change in OD 350 nm of the protein in the presence of the excipient and $\Delta OD_{350}$ (C) the change in OD 350 nm of the protein without excipient (Peek et al., Journal of Pharmaceutical Sciences 96(1):44-60, 2006).

Structural Stability Studies.

Toxoid solutions were studied at a concentration of 0.2 mg/ml for CD measurements and 0.1 mg/ml for fluorescence and UV absorption analysis. No concentration dependence was seen over this range. Each sample was evaluated in duplicate to ensure reproducibility of the measurements.

Far-UV Circular Dichroism (CD) Spectroscopy.

CD spectra were acquired using a Jasco J-810 spectropolarimeter equipped with a 6-position Peltier temperature controller. CD spectra were obtained from 260-190 nm with a scanning speed of 20 nm/minute, an accumulation of 2 and a 2 second response time. The CD signal at 208 nm was monitored every 0.5° C. over a 10 to 85° C. temperature range employing a temperature ramp of 15° C./hour to study thermal transitions (melting curves) of the proteins (in sealed cuvettes with 0.1 cm pathlength). The CD signal was converted to molar elipticity by Jasco Spectral Manager software. The midpoint temperature of the thermal transition was obtained from a sigmoid fitting of the melting curves using Origin software.

ANS Fluorescence Spectroscopy.

Accessibility of apolar sites on the proteins was monitored by fluorescence emission of the extrinsic probe 8-Anilino-1-naphthalene sulfonate (ANS). Each sample contained a 20-fold molar excess of ANS to protein. The emission spectra were collected from 400 to 600 nm with a step size of 2 nm and a 1 second integration time after ANS excitation at 372 nm. Emission spectra were collected every 2.5° C. with 5 minutes of equilibration over a temperature range of 10 to 85° C. The ANS-buffer baseline at each corresponding pH was subtracted from the raw emission spectra. Peak positions of the emission spectra were obtained from polynomial fits using Origin software.

High-Resolution UV Absorbance Spectroscopy.

High-resolution UV absorbance spectra were acquired using an Agilent 8453 UV-visible spectrophotometer. Aggregation of the proteins was studied by monitoring the OD at 350 nm every 2.5° C. over the temperature range of 10 to 85° C. with a 5 minute incubation (sufficient for equilibrium to be reached) at each temperature.

Dynamic Light Scattering.

The mean hydrodynamic diameter of the proteins at pH 6.5 (alone and in presence of excipients) was analyzed using a dynamic light scattering instrument (Brookhaven Instrument Corp., Holtzille, N.Y.). The instrument was equipped with a 50 mW diode-pumped laser ($\lambda$=532 nm) and the scattered light was monitored at 90° to the incident beam. The autocorrelation functions were generated using a digital auto-correlator (BI-9000AT). The hydrodynamic diameter was calculated from the diffusion coefficient by the Stokes-Einstein equation using the method of cumulants (lognormal number based). The data was fit to a non-negatively constrained least squares algorithm to yield multi-modal distributions (MSD). The instrument was equipped with a temperature-controlled circulating water bath RTE111 (Neslab, Newington, N.H.) and the hydrodynamic diameter was monitored over a temperature range of 10 to 85° C.

Differential Scanning Calorimetry (DSC).

DSC was performed using a MICROCAL VPDSC with autosampler (MicroCal, LLC; Northampton, Mass.). Thermograms of toxoids (0.5 mg/ml) alone and in the presence of excipient(s) were obtained from 10-90° C. using a scan rate of 60° C./hour. The filled cells were equilibrated for 15 minutes at 10° C. before beginning each scan. Thermograms of the buffer alone were subtracted from each protein scan prior to analysis.

Agitation Studies.

Toxoid solutions at a concentration of 0.4 mg/ml were studied in the presence and absence of the excipients. Protein samples (0.4 ml) were placed in 1.5 ml centrifuge tubes and shaken in a rotator (THERMOMIXER®, Eppendorf AG, Hamburg, Germany) at 300 rpm for 72 hours at a constant temperature of 4° C. The concentration of the protein and OD 350 nm were measured before and after the rotation to evaluate adsorption to vessel walls and aggregation. Samples were centrifuged for 10 minutes at a speed of 10,000×g at 4° C. and the concentration and OD 350 nm of the supernatant were measured to detect formation of insoluble aggregates. The structures of the proteins were evaluated by CD. Each sample was measured in duplicate.

Adjuvant Studies

Adsorption to Aluminum Hydroxide (ALHYDROGEL®) (Aluminum Hydroxide Adjuvant).

The ability of the toxoids to adsorb to ALHYDROGEL® (Brenntag Biosectror, Frederickssund, Denmark; aluminum hydroxide adjuvant) at various concentration (0.025-1 mg/ml) was determined by constructing a binding isotherm. The protein solutions in the presence of 0.4 mg/ml ALHYDROGEL® (aluminum hydroxide adjuvant) were tumbled in an end-over-end tube rotator at refrigerator temperature for 20 minutes. The samples were centrifuged at 14,000×g for 30 seconds to pellet the adjuvant. The value of the concentration of the protein remaining in the supernatants was used for the construction of binding curves. The ability of protein to bind to the ALHYDROGEL®(aluminum hydroxide adjuvant) in the presence of excipients was determined by the same procedure. In this case, the ALHYDROGEL® (aluminum hydroxide adjuvant) was added to the protein-excipient solution.

Desorption of toxoids from ALHYDROGEL® (aluminum hydroxide adjuvant). Desorption of the proteins from ALHYDROGEL® (aluminum hydroxide adjuvant) was evaluated in presence of 2 M NaCl. The toxoid ALHYDROGEL® (aluminum hydroxide adjuvant) pellets were prepared as described above. The pellets were washed with buffer (pH 6.5) to remove protein present in the supernatant prior to addition of the NaCl solution. The ALHYDROGEL® (aluminum hydroxide adjuvant) solutions were tumbled in an end-over-end tube rotator at refrigerator temperature for 20 minutes. The samples were centrifuged at 14,000×g for 30 seconds to pellet the adjuvant. The concentration of the protein in the supernatants was used for the construction of desorption isotherms.

Stability of Toxoids Bound to ALHYDROGEL® (Aluminum Hydroxide Adjuvant).

The thermal stability of the toxoids bound to ALHYDROGEL® (aluminum hydroxide adjuvant) was monitored with DSC using a MICROCAL VP-AutoDSC (MicroCal, LLC, Northampton, Mass.). Toxoids at 0.5 mg/ml were bound to 0.4 mg/ml ALHYDROGEL® (aluminum hydroxide adjuvant) by the procedure described above. Thermorgams of the toxoids were obtained from 10 to 90° C. with a scanning rate of 60° C./hour. The samples were equilibrated for 15 minutes at 10° C. before each scan. Thermograms of the ALHYDROGEL® (aluminum hydroxide adjuvant) alone were subtracted from each protein/adjuvant scan prior to analysis.

Results and Discussion

Excipient Screening Studies

To investigate the ability of GRAS compounds to prevent/delay aggregation, toxoids were incubated alone and in presence of excipients under stress conditions (incubation at 55° C.). Aggregation of the toxoids was monitored in a high-throughput fashion by monitoring changes in OD at 350 nm during the incubation time. The turbidity changes were further used to calculate % of aggregation inhibition and are summarized in Table 1 for toxoid A and Table 2 for toxoid B.

High-throughput aggregation assays of toxoid A found that more than half of the excipients either delayed or prevented increases of OD 350 nm over time and led to inhibition of aggregation by 90% or more (Table 1). Among the excipients examined, 2.5% albumin, 2.5% a-cyclodextrin, 0.1% TWEEN 80, 0.3 M histidine, and 0.3 M lysine led to instantaneously high OD 350 nm values, which suggests that toxoid A is insoluble under these conditions. The aggregation of toxoid A was also significantly enhanced in presence of 16 other excipients, among which 25 and 50 mM arginine/glutamine mixture, 0.3 M arginine, and 0.3 M proline were especially potent.

Inhibition of toxoid B aggregation by 90% or more occurred in presence of 15 excipients (Table 2). The presence of 0.3 M histidine or 0.2 M sodium citrate led to instantaneously high OD 350 nm. Another 20 compounds more gradually induced aggregation during the time monitored. Extremely high increases in OD 350 nm were observed in presence of 0.015 M calcium chloride, 0.15 M ascorbic acid, and 0.3 M arginine.

In many cases, the aggregation of both toxoids was facilitated by the same excipients (Tables 1 and 2). In contrast, 5% 2-OH propyl y-CD, 0.01% and 0.1% TWEEN 20, 0.15 M aspartic acid, and 0.3 M guanidine facilitated aggregation of toxoid B alone. In addition, aggregation in the presence of 0.015 M calcium chloride was much greater for toxoid B than toxoid A. This may be related to the known increased thermal stability of the toxin A C-terminal domain in the presence of calcium chloride (Demarest et al., Journal of Molecular Biology 346(5):1197-1206, 2005). The dissimilarities between the toxoids in their responses to solute induced aggregation is presumably related to structural differences between the corresponding toxins (Warny et al., Lancet 366(9491):1079-1084, 2005; Just et al., Reviews of Physiology, Biochemistry and Pharmacology 152:23-47, 2005). An absence of inositolphosphates among compounds studied suggests that the observed aggregation of the toxoids does not involve autocatalytic cleavage (Reineke et al., Nature (London, United Kingdom) 446(7134):415-419, 2007). Most of the carbohydrates, detergents, and cyclodextrins examined inhibited aggregation of the toxoids. The following excipients were found to efficiently inhibit aggregation of both of the toxoids: 20% trehalose, 20% sucrose, 10% sorbitol, 10% dextrose, and 20% glycerol.

The above-mentioned carbohydrates, sorbitol, glycerol, and two surfactants (0.05%/0.1% TWEEN 80 and 0.1% PLURONIC F-68) were further studied for their ability to stabilize the secondary and tertiary structure of the proteins at pH 6.5 by monitoring ANS fluorescence, CD signal changes upon heating, and DSC (FIGS. 1 and 2). Toxoid A in the presence of 20% sucrose and 20% trehalose produced an earlier onset of secondary structure change, whereas the rest of the excipients delayed the thermal transition by ~2° C. (FIG. 1*a*). Surprisingly, toxoid B manifested an earlier onset of secondary structure change only in presence of 20% sucrose, while the rest of the excipients delayed the thermal transition by ~1° C. (FIG. 2*a*). The early onset of the secondary structure change of the toxoids in the presence of trehalose and/or sucrose could be explained by stabilization of partially unfolded state(s) by the solutes. Additionally, the possibility that the toxoids are partially unfolded upon binding to their C-terminal carbohydrate recognition sequence repeats by polysaccharides (Greco et al., Nature Structural & Molecular Biology 3(5):460-461, 2006) cannot be ruled out. In the case of the structural destabilization by the second mechanism, the dissimilarity of the behavior of the two toxoids in the presence of trehalose could be related to structural differences between toxoids (the C-terminal domain possesses 30 repeats in toxoid A and 19 repeats in toxoid B; Just et al., Reviews of Physiology, Biochemistry and Pharmacology 152:23-47, 2005). It is interesting to note that the monosaccharide (dextrose) had a stabilizing effect on the secondary structure of both toxoids. Temperature induced unfolding of both toxoids and associated binding of ANS was not influenced by the presence of the compounds (FIG. 1*b*, 2*b*). The effect of the detergents on the temperature-induced unfolding of the toxoids was monitored with DSC and did not appear to be significant (FIG. 1*c*, 2*c*, and Table 3). These observations suggest that the excipients do not strongly stabilize the structure of the toxoids by the well described preferential exclusion mechanism, but rather inhibit their aggregation by other mechanisms, such as direct blocking of the protein/protein interactions that are responsible for protein association (Timasheff, Proc. Natl. Acad. Sci. U.S.A. 99(15):9721-9726, 2002; Timasheff, Advances in Protein Chemistry 51(Linkage Thermodynamics of Macromolecular Interactions):355-432, 1998).

Figure 3A:
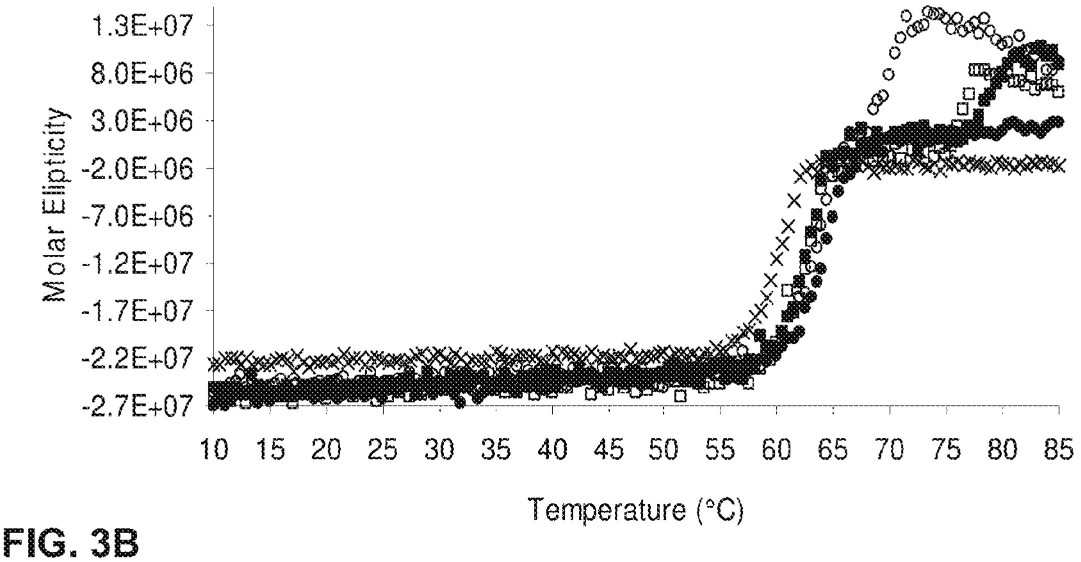
FIG. 3. Studies of the effect of combinations of solutes on the thermal stability of toxoid A (x) in presence of 10% sorbitol and 0.05% TWEEN 80 (□), 10% dextrose and 0.05% TWEEN 80 (■), 10% sorbitol, 10% dextrose and 0.05% TWEEN 80 (○), 10% dextrose and 10% sorbitol (●): (a) monitored by the CD signal at 208 nm and (b) OD 350 nm. The thermal traces represent an average of 2 measurements, in which each data point had a standard error of less than 0.05.
Figure 3B:
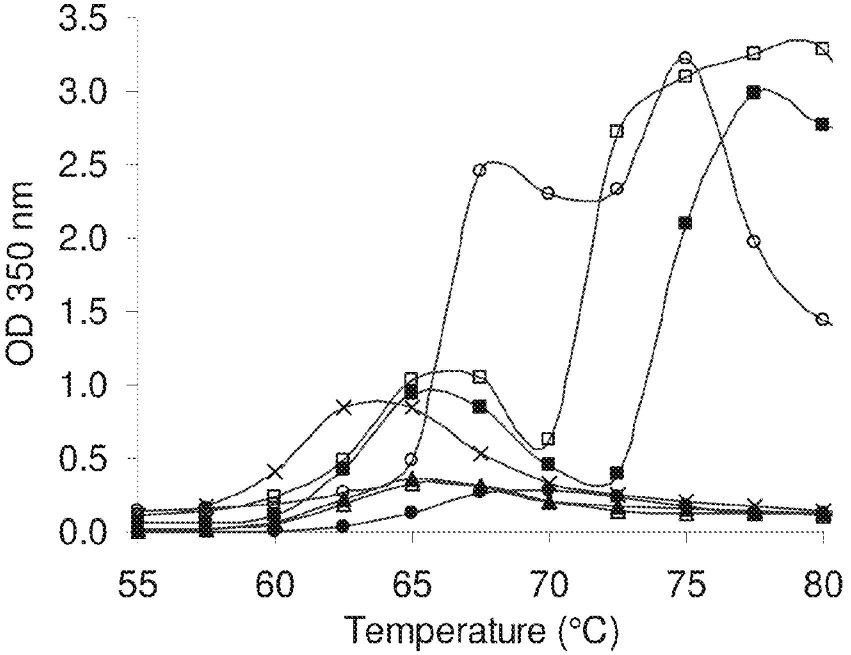
Figure 4A:
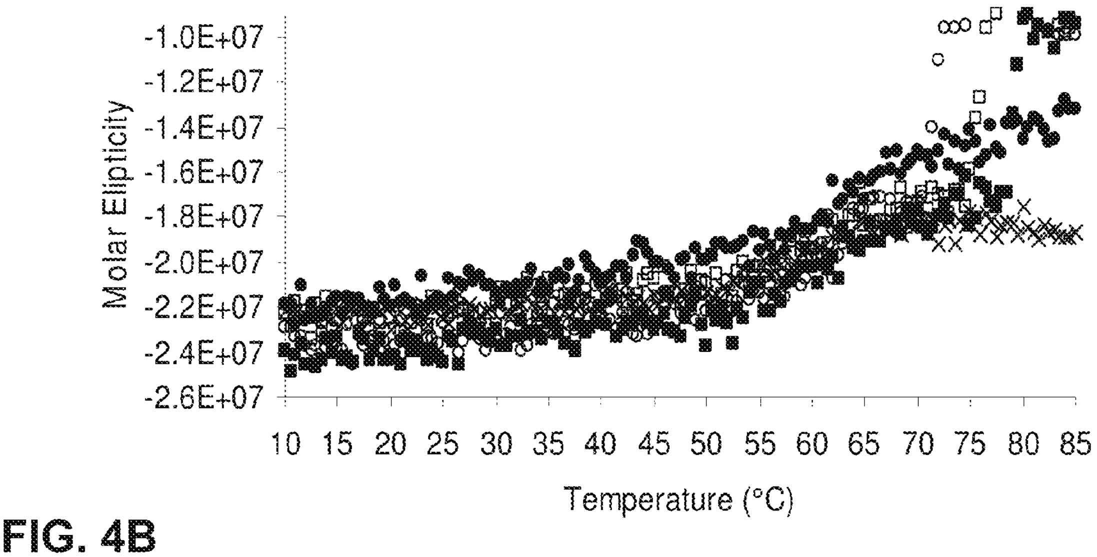
FIG. 4. Studies of combinations of solutes and their effects on the thermal stability of toxoid B (x) in presence of 10% sorbitol and 0.05% TWEEN 80 (□), 10% dextrose and 0.05% TWEEN 80 (■), 10% sorbitol, 10% dextrose, and 0.05% TWEEN 80 (○), 10% dextrose and 10% sorbitol (●): (a) monitored by CD signal at 208 nm and (b) OD 350 nm. The thermal traces represent an average of 2 measurements, where each data point had standard error of less than 0.05.
Figure 4B:
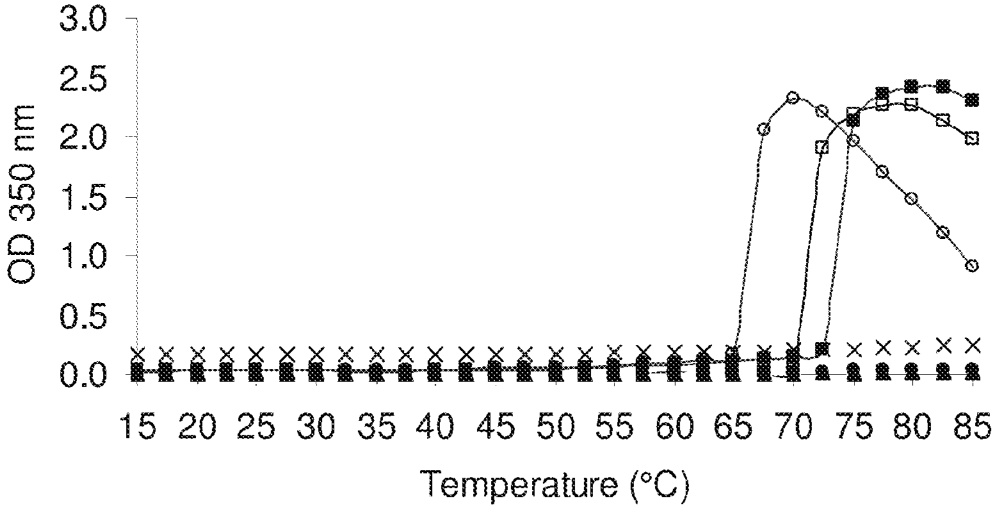
Figure 5A:
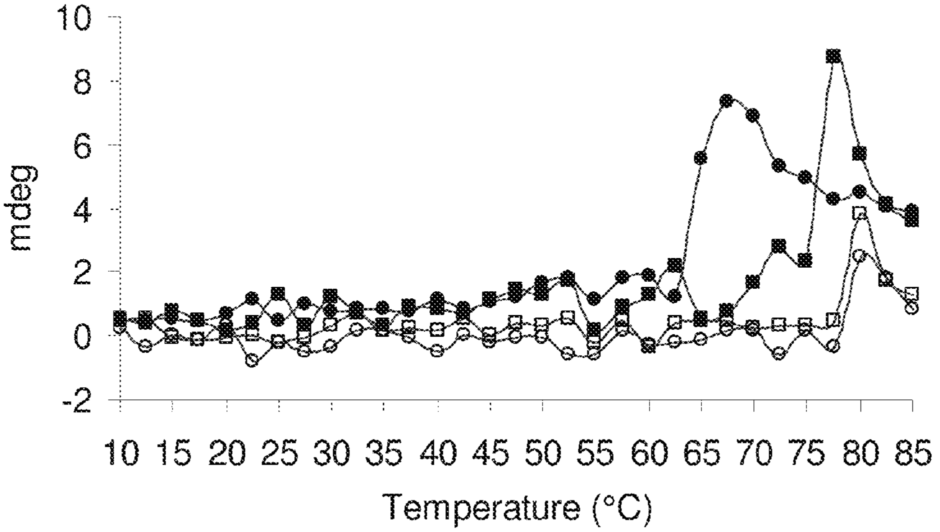
FIG. 5. Studies of the properties of TWEEN 80 (□) in presence of 10% dextrose (■), 10% sorbitol (○), 10% dextrose and 10% sorbitol (●) as a function of temperature: 208 nm CD signal of 0.05% TWEEN 80 (a) and 0.1% TWEEN 80 (b); OD 350 nm for 0.05% tween 80 (c) and 0.1% TWEEN 80 (d); hydrodynamic diameter MSD Number based (filled square) and Lognormal Number based (filled rhomb) for 0.05% TWEEN 80 (e) and 0.1% TWEEN 80 (f). Sizes of >1 μm are not accurate given the nature of DLS measurements. The thermal traces represent an average of 2 measurements, where each data point had standard error of less than 0.5.
Figure 5B:
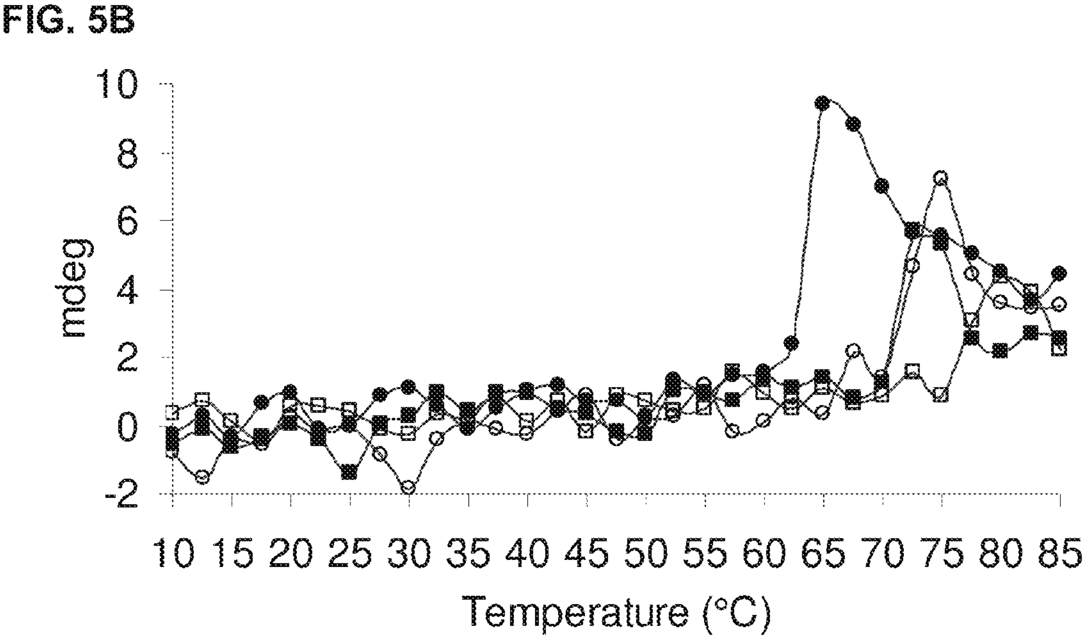
Figure 5C:
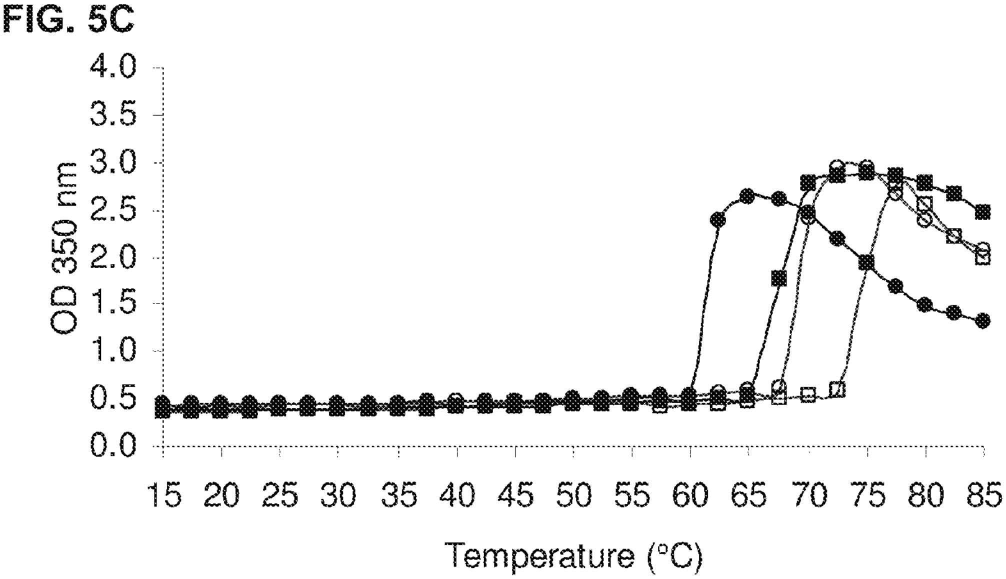
Figure 5D:
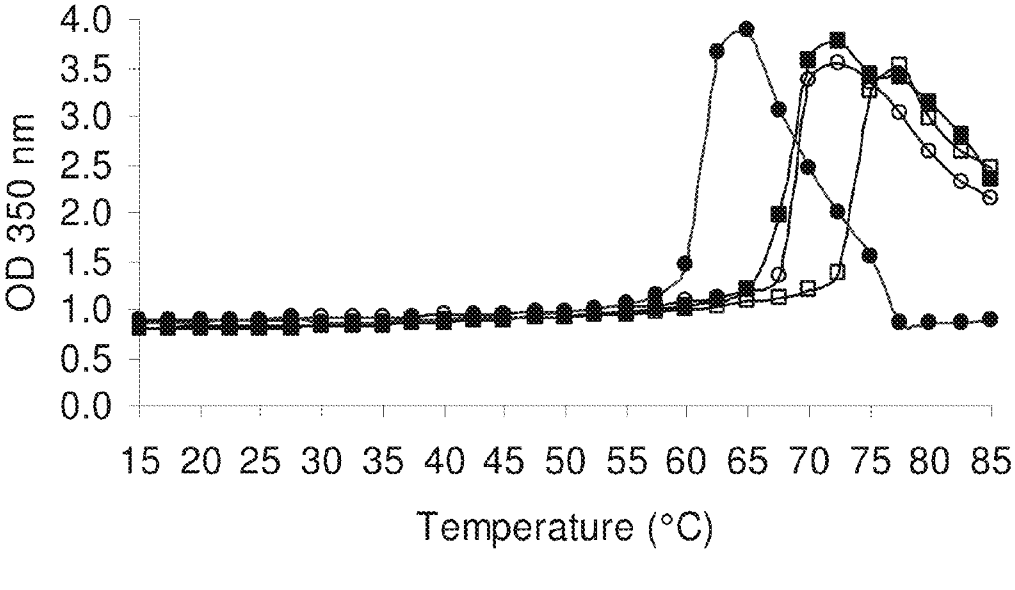
Figure 5E:
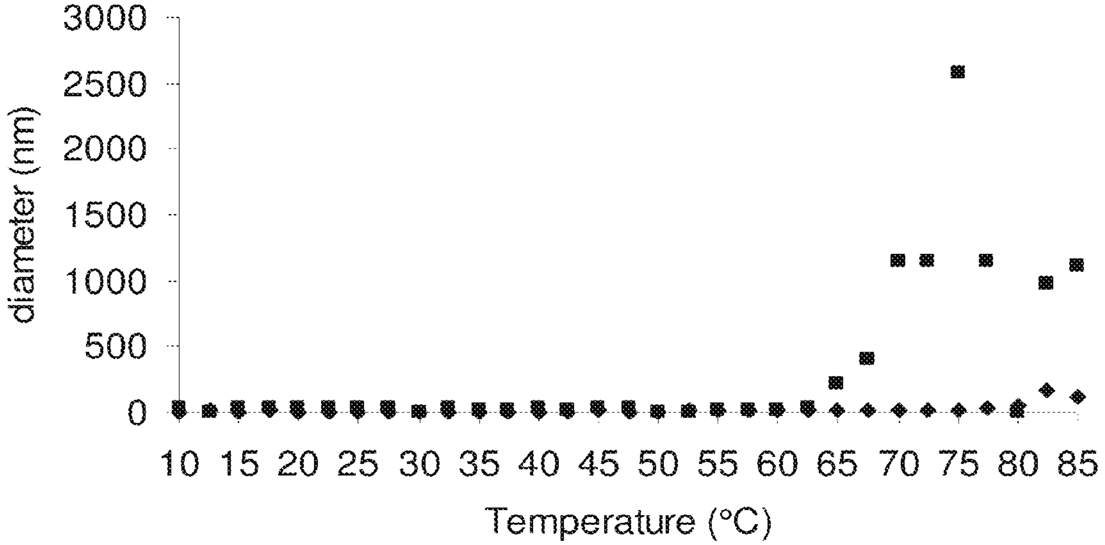
Figure 5F:
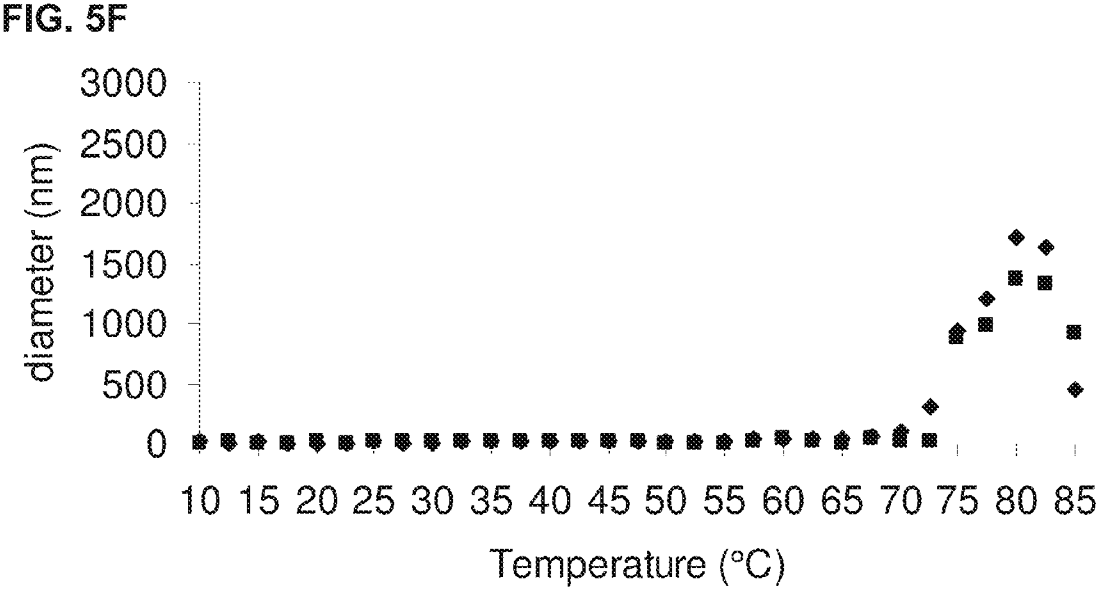
Figure 6A:
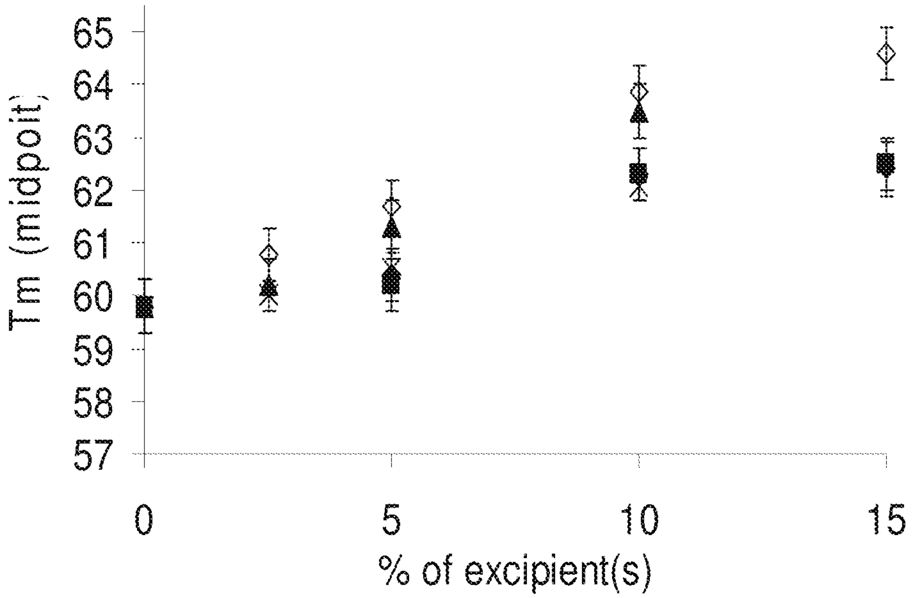
FIG. 6. Studies of the effect of solute concentration on the midpoint of the thermal transition (Tm) monitored with CD 208 nm signal for toxoid A (a) and toxoid B (b) in presence of sorbitol and 0.05% TWEEN 80 (◇), dextrose and 0.05% TWEEN 80 (■), sorbitol, dextrose, and 0.05% TWEEN 80 (▲), sorbitol, dextrose, and 0.1% TWEEN 80 (x), sorbitol and dextrose (0).
Figure 6B:
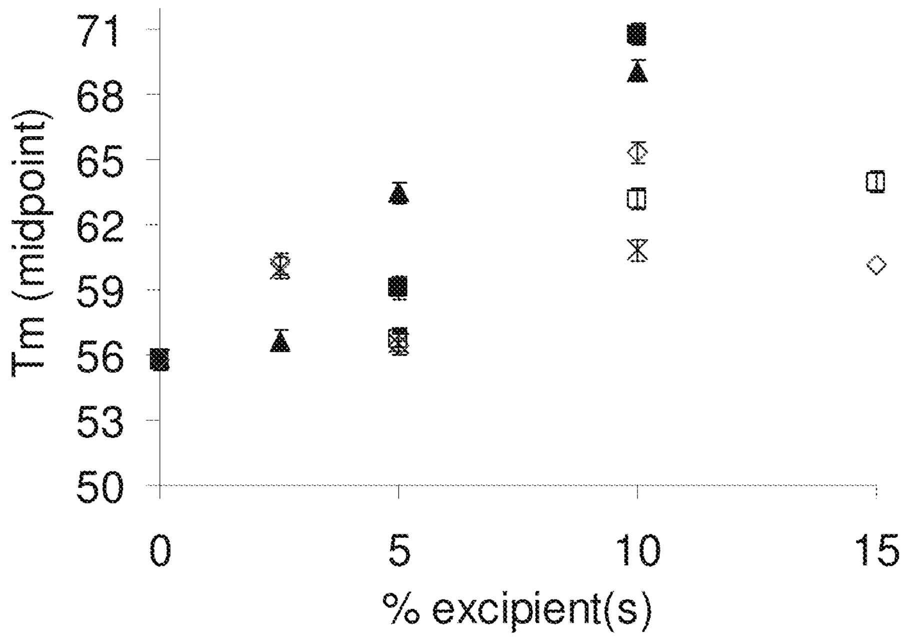
Figure 7A:
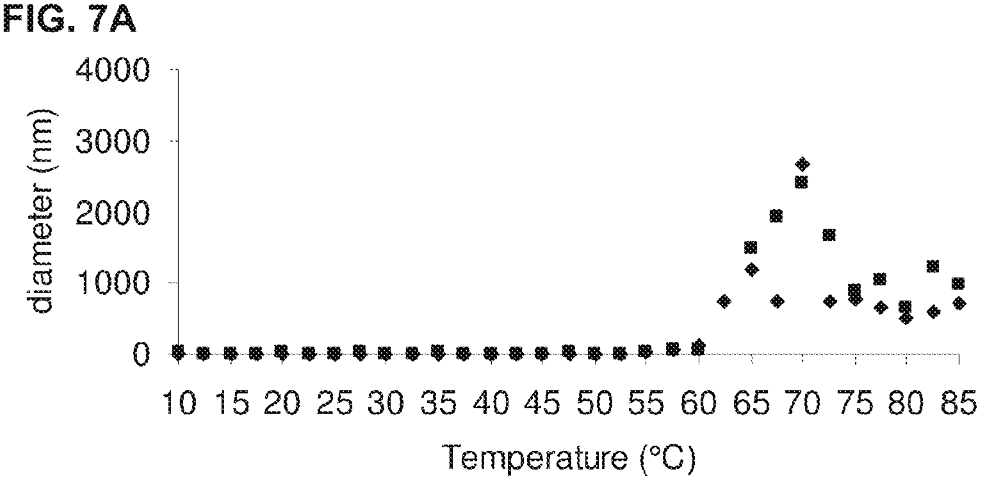
FIG. 7. The hydrodynamic diameter as a function of temperature for toxoid A (a-c) and toxoid B (d-f) where the filled squares represent MSD number based diameter and filled rhomboids represent the lognormal number based diameter. Sizes of >1 μm are not accurate given the nature of DLS measurements. (a,d) protein alone; (b,e) protein in presence of 10% sorbitol and 10% dextrose; (c,f) protein in presence of 10% sorbitol, 10% dextrose and 0.05% TWEEN 80. The thermal traces represent an average of 2 measurements, where each data point had a standard error of less than 0.5.
Figure 7B:
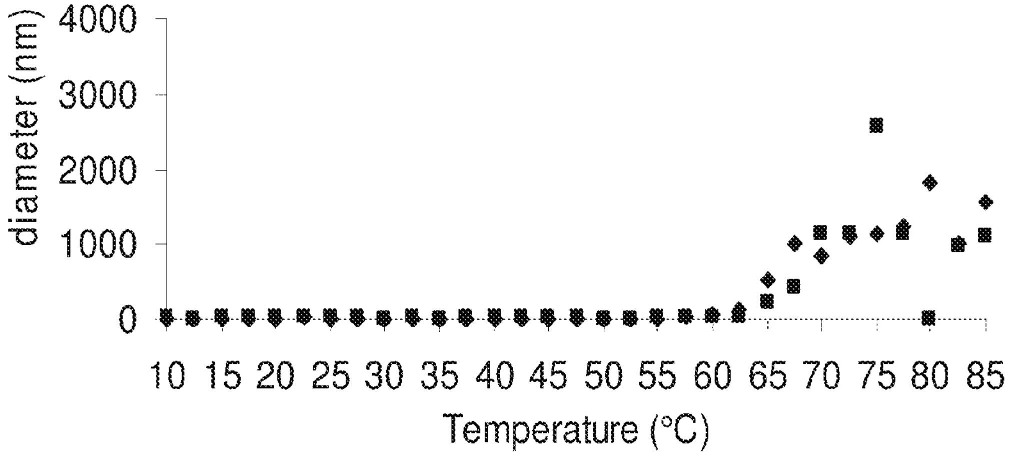
Figure 7C:
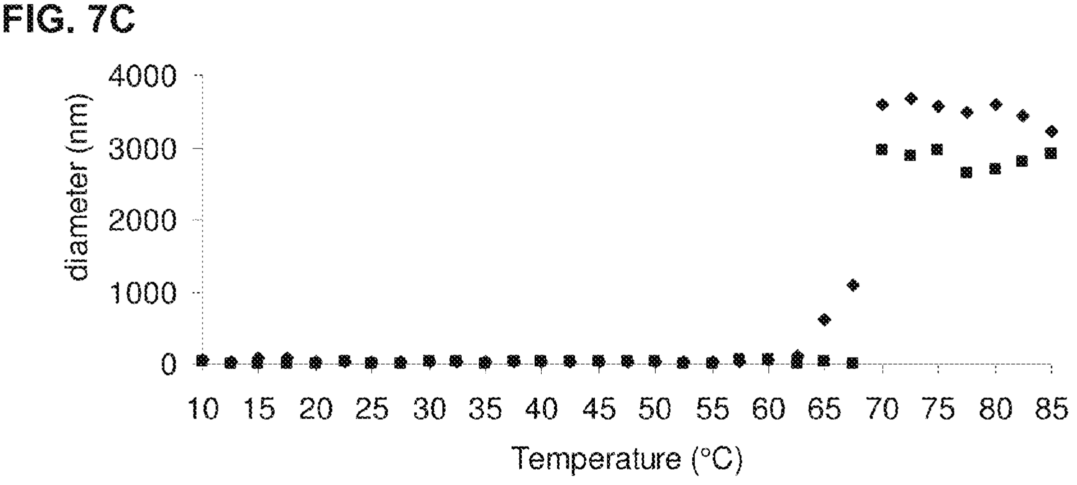
Figure 7D:
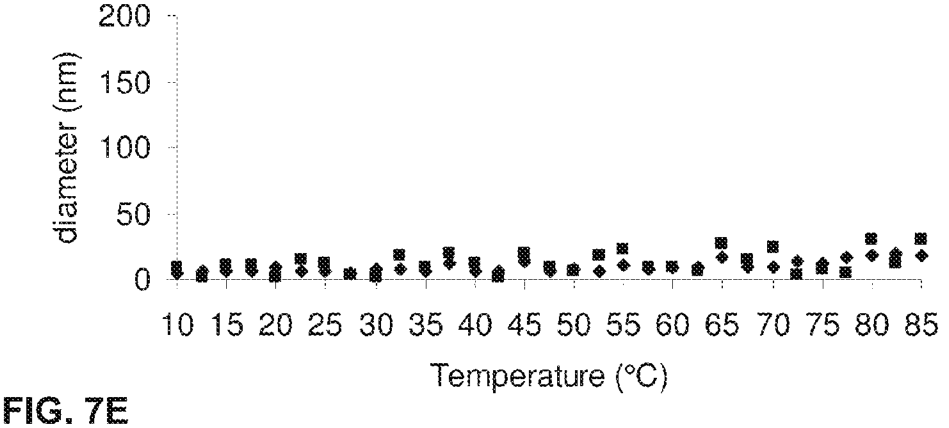
Figure 7E:
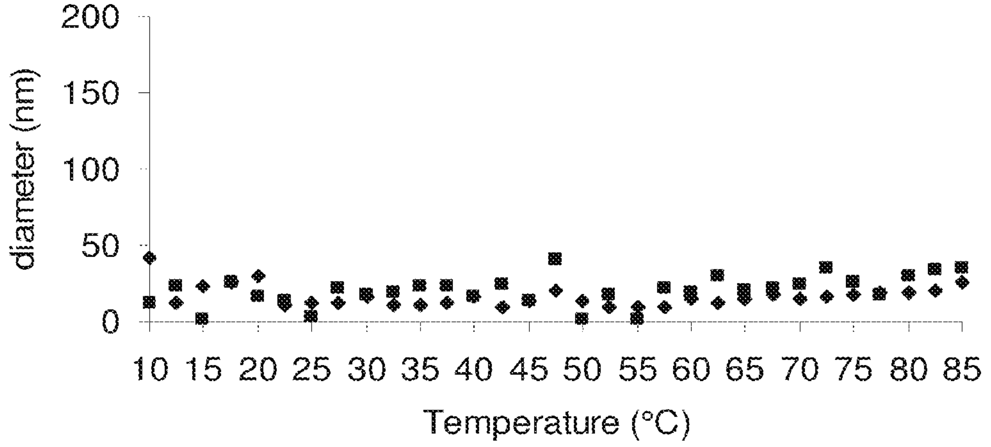
Figure 7F:
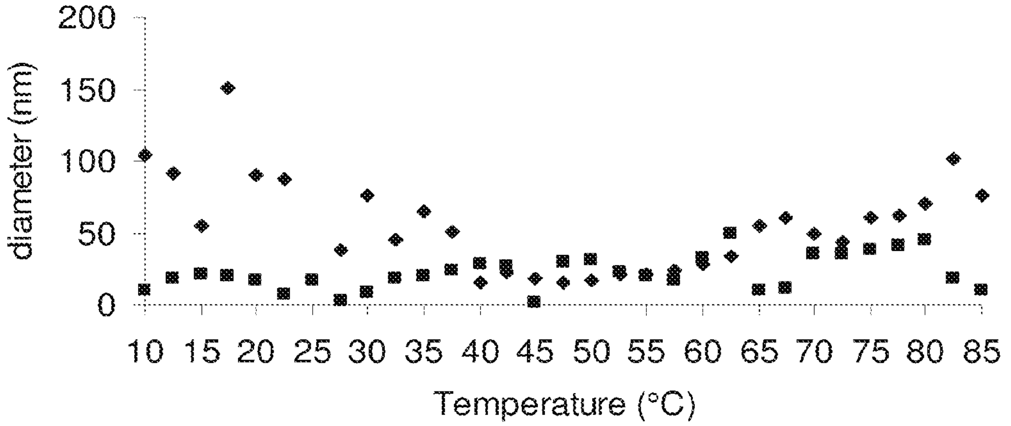

To study the effect of a combination of the more active agents on secondary structure, the results from a mixture of sorbitol, dextrose, and TWEEN 80 were characterized by monitoring the thermal transitions of the toxoids with CD and aggregation with OD 350 nm (FIGS. 3 and 4). The heating of solutions of TWEEN 80 (0.05% or 0.1%) alone or in the presence of sorbitol and/or dextrose led to changes in its micelle structure, which were manifested by a decrease in the CD signal and increased light scattering as monitored by OD 350 nm (FIG. 5). The concentration of the excipients had an approximately linear effect on the temperature of the thermal transitions (FIG. 6). This supports the hypothesis that the excipients prevent aggregation by directly inhibiting protein association. The effects of the excipients on the thermal transition are summarized in Tables 4 and 5. The combination of 10% dextrose and 10% sorbitol in the presence or absence of 0.05% TWEEN 80 tends to delay the midpoint of the thermal transition of both the toxoids to the greatest extent (~4° C. for toxoid A and ~10° C. for toxoid B) (FIG. 3). This can be explained by either a synergistic effect and/or the higher total concentration of the stabilizing compounds. In the case of toxoid B, the onset temperature of the transition was not delayed in presence of the combination of agents, but the midpoint of the thermal transition was significantly delayed. This could be related to a more gradual unfolding of toxoid B in the presence of the two or more excipients. Toxoid A manifested a significant delay of aggregation (monitored with OD 350 nm) in presence of stabilizing compounds (FIG. 4*a*). The hydrodynamic diameter of the toxoids in the presence and absence of the excipients was also monitored by DLS (FIG. 7). Toxoid A manifested a delayed onset of the previously observed hydrodynamic diameter increase in the presence of the excipients (FIG. 7*a-c*), whereas a smaller effect was seen with toxoid B (FIG. 7*d-f*). These observations suggest that the particular combination of potential vaccine excipients tested here stabilizes protein structure by both a preferential hydration mechanism and direct inhibition of protein association. The use of such stabilizing compounds could potentially increase the physical stability of the toxoids during storage.

Agitation Studies

The effect of agitation on toxoid physical stability was studied by monitoring protein adsorption to the walls of storage vials, formation of insoluble aggregates, and changes in protein thermal stability. An insignificant change in protein concentration, OD 350 nm, and in CD melts in the presence and absence of the excipients indicated that the toxoids do not undergo major physical changes upon application of this agitation-based stress.

Adjuvant Studies

Figure 8A:
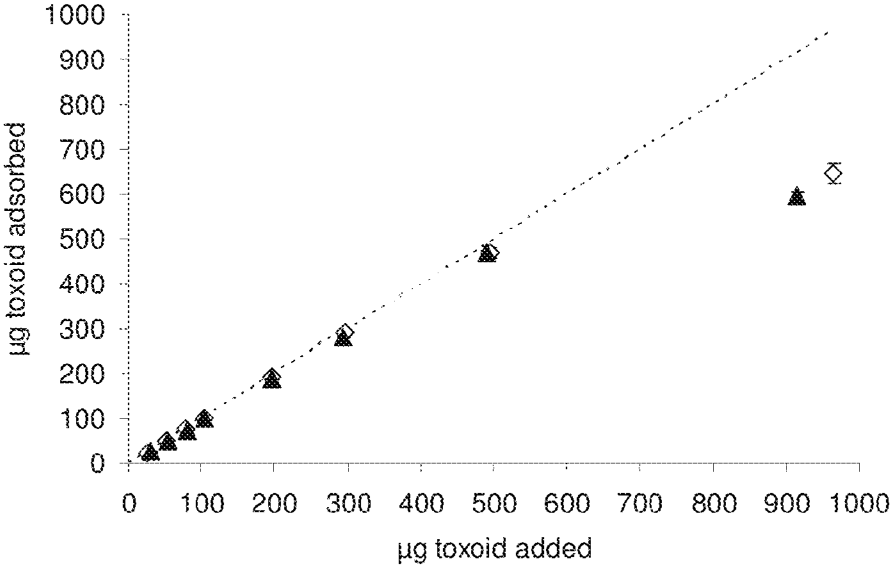
FIG. 8. ALHYDROGEL® (aluminum hydroxide adjuvant) binding studies: (a) adsorption isotherm and (b) desorption isotherm in presence of 2 M NaCl for toxoid A (◇) and toxoid B (▲).
Figure 8B:
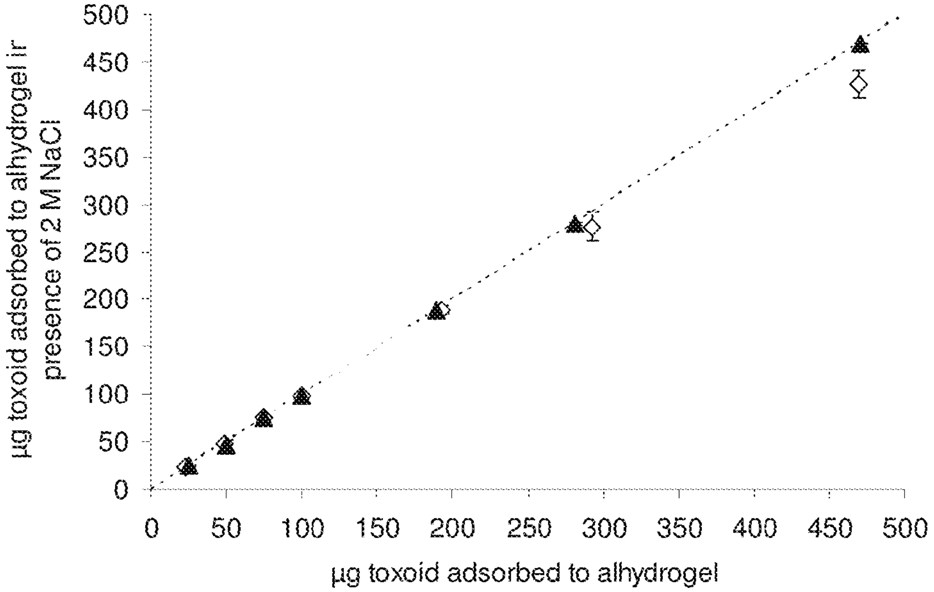

Adjuvant binding isotherms revealed that the toxoids efficiently bind to ALHYDROGEL® (aluminum hydroxide adjuvant) at low concentrations with binding saturated at higher protein concentration (FIG. 8*a*). The toxoids at 0.5 mg/ml are 95% or more bound to ALHYDROGEL® (aluminum hydroxide adjuvant), which allows use of DSC to directly monitor the stability of protein on the surface of the adjuvant. The absence of toxoids desorption upon addition of 2 M NaCl indicates that the interaction of toxoids with ALHYDROGEL® (aluminum hydroxide adjuvant) is not solely electrostatic as is often observed in protein/Aluminum hydroxide interactions (FIG. 8*b*; Gupta et al., Pharmaceutical Biotechnology 6:229-248, 1995; Seeber et al., Vaccine 9(3):201-203, 1991; White et al., Developments in Biologicals (Basel, Switzerland) 103(Physico-Chemical Procedures for the Characterization of Vaccines):217-228, 2000).

Upon binding to ALHYDROGEL® (aluminum hydroxide adjuvant), toxoid A manifests no detectable change in its thermal stability, whereas adjuvant-bound toxoid B demonstrates a decrease of the Tm by ~1.4° C. The fraction of ALHYDROGEL® (aluminum hydroxide adjuvant) bound toxoid is somewhat reduced in the presence of most of the excipients (Table 6 and 7). This suggests that the excipients partially interfere with toxoid binding to ALHYDROGEL® (aluminum hydroxide adjuvant) perhaps by direct interaction with either the protein and/or adjuvant. The thermal stability of the proteins bound to ALHYDROGEL® (aluminum hydroxide adjuvant) in the presence and absence of the excipients is summarized in Table 6 for toxoid A and Table 7 for toxoid B. The presence of the excipients perturbed the thermal stability of adjuvant-bound toxoids either by decreasing or increasing the transition temperature. A decrease of thermal stability was seen in both toxoids in presence of 10% sorbitol, whereas the presence of 10% sorbitol and 10% dextrose decreases the thermal stability of toxoid B alone. Additionally, TWEEN 80 had a stabilizing effect only in case of adjuvant-bound toxoid B. On the other hand, dextrose (10%) had a stabilizing effect on the thermal stability of both toxoids. Interestingly, the combination of the three excipients (10% sorbitol, 10% dextrose, with 0.05% or 0.1% TWEEN 80) tends to raise the thermal transition of both adjuvant-bound toxoids by 3-4° C.

Conclusions

A systematic approach to stabilizer screening resulted in the identification of excipients that improved the thermal stability of both the A and B *Clostridium difficile* toxoids. Studies of ALHYDROGEL® (aluminum hydroxide adjuvant) bound toxoids in the presence of selected excipients identified conditions that produced improved physical stability of the adjuvant-bound proteins. This study also generated information concerning the physical behavior of the toxoids under a range of conditions (temperature, solute) that can be used to design formulations of enhanced storage stability.

Example II

Additional changes to the formulation of the *C. difficile* toxoid vaccine were investigated in an effort to improve the stability and immunogenicity profiles of the vaccine. Preclinical and clinical data generated with the vaccine to-date indicated that increased stability and immunogenicity profiles would be important to support future clinical studies.

pH

Determining a pH that yields the maximum stability was part of the formulation improvement effort. Studies were performed on liquid samples held at −65° C., 5° C., 25° C., and 37° C. for up to 28 days with pH ranging from 5.5-7.5. The following methods were employed to establish the stability profile:

1. circular dichroism (CD) spectroscopy (changes in secondary structure), 2. circular dichroism (CD) spectroscopy (changes in melting temperature, $T_m$), and 3. spectrophotometry ($OD_{350\ nm}$) and SEC-HPLC (aggregate formation).

Figure 9:
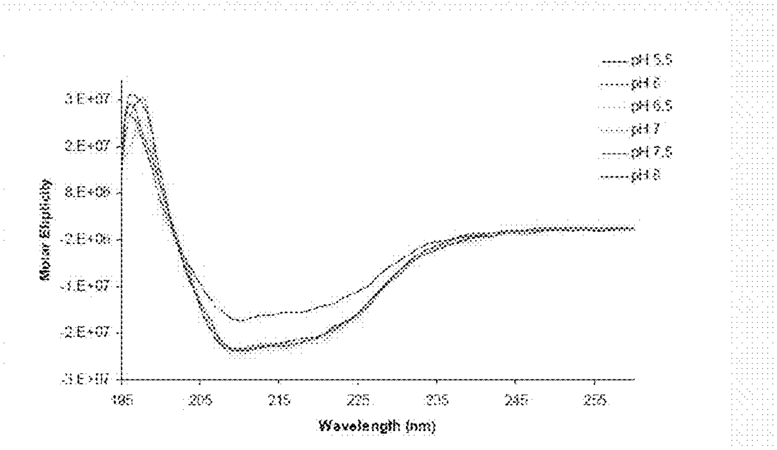
FIG. 9. Study of secondary structure of toxoid A by circular dichroism (CD) spectroscopy over pH range of 5.5 to 7.5.
Figure 10:
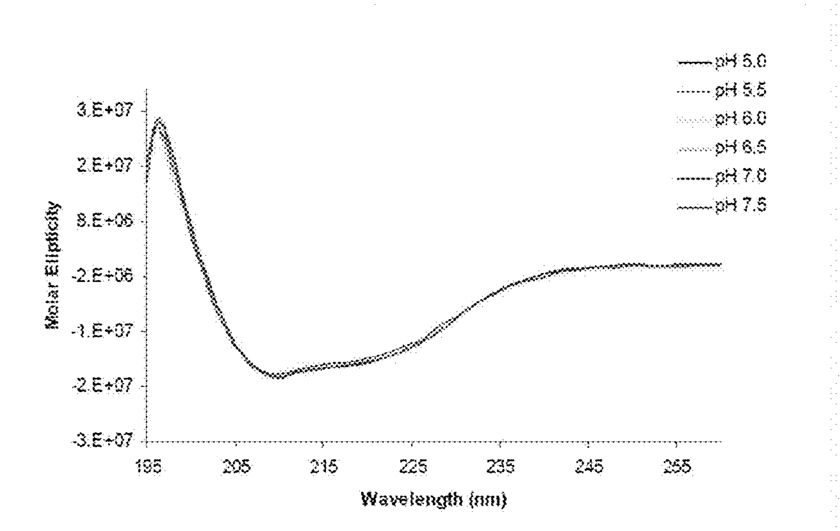
FIG. 10. Study of secondary structure of toxoid B by circular dichroism (CD) spectroscopy over pH range of 5.5 to 7.5.
Figure 11:
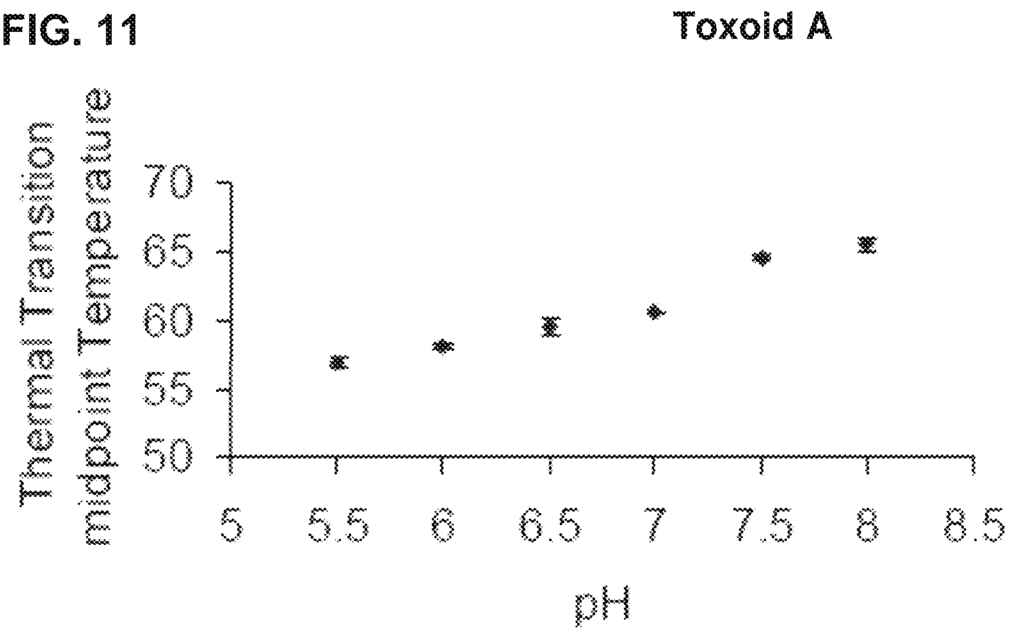
FIG. 11. Study of melting temperature of toxoid A by circular dichroism (CD) spectroscopy over pH range of 5.5-8.0.
Figure 12:
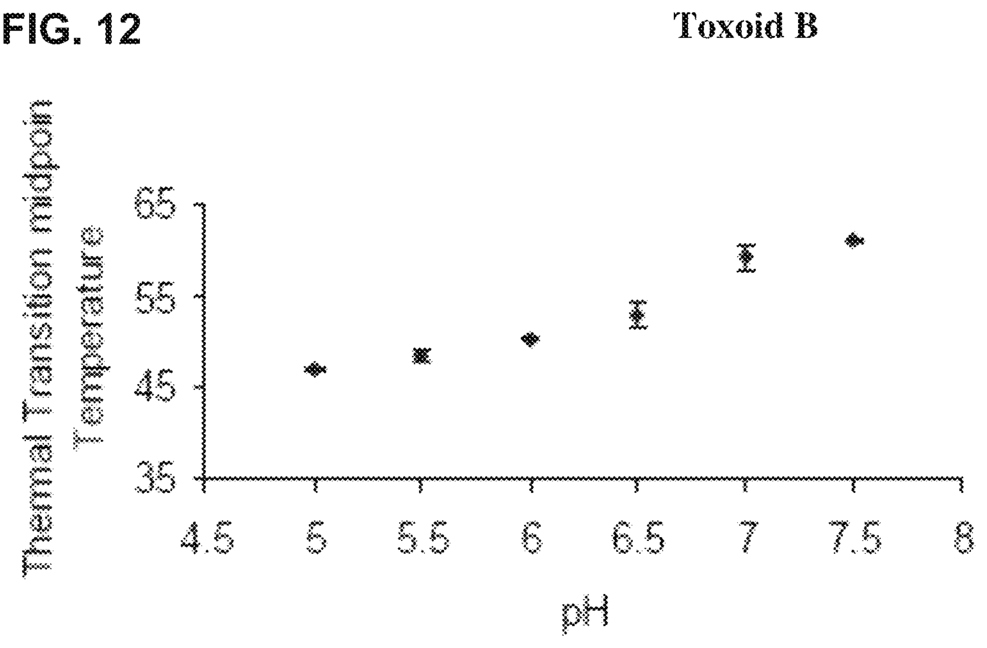
FIG. 12. Study of melting temperature of toxoid B by circular dichroism (CD) spectroscopy over pH range of 5.0-7.5.

There was no change in secondary structure observed in the CD spectrum for toxoid A above pH 6.0 and for toxoid B across the entire pH range tested (FIG. 9 and FIG. 10; Salnikova et al., J. Pharm. Sci. 97(9):3735-3752, 2008). The melting point data acquired from the CD measurements revealed that the maximum stability of both toxoids is at a pH of greater than 7.0 (FIG. 11 and FIG. 12).

The toxoid A and B aggregation states across a pH range of 6-7.5 varied little in the range of ≤−60° C., when analyzed by SEC-HPLC for aggregate formation (% monomer) and % area recovery. However, differences in aggregation states became more apparent across the pH range when temperatures were elevated (particularly above 5° C.), with the lower pH values trending toward greater shifts in aggregation levels. This is accompanied by an increase in optical density at 350 nm at lower pH values, as described in Salnikova et al., J. Pharm. Sci. 97(9):3735-3752, 2008.

Figure 13:
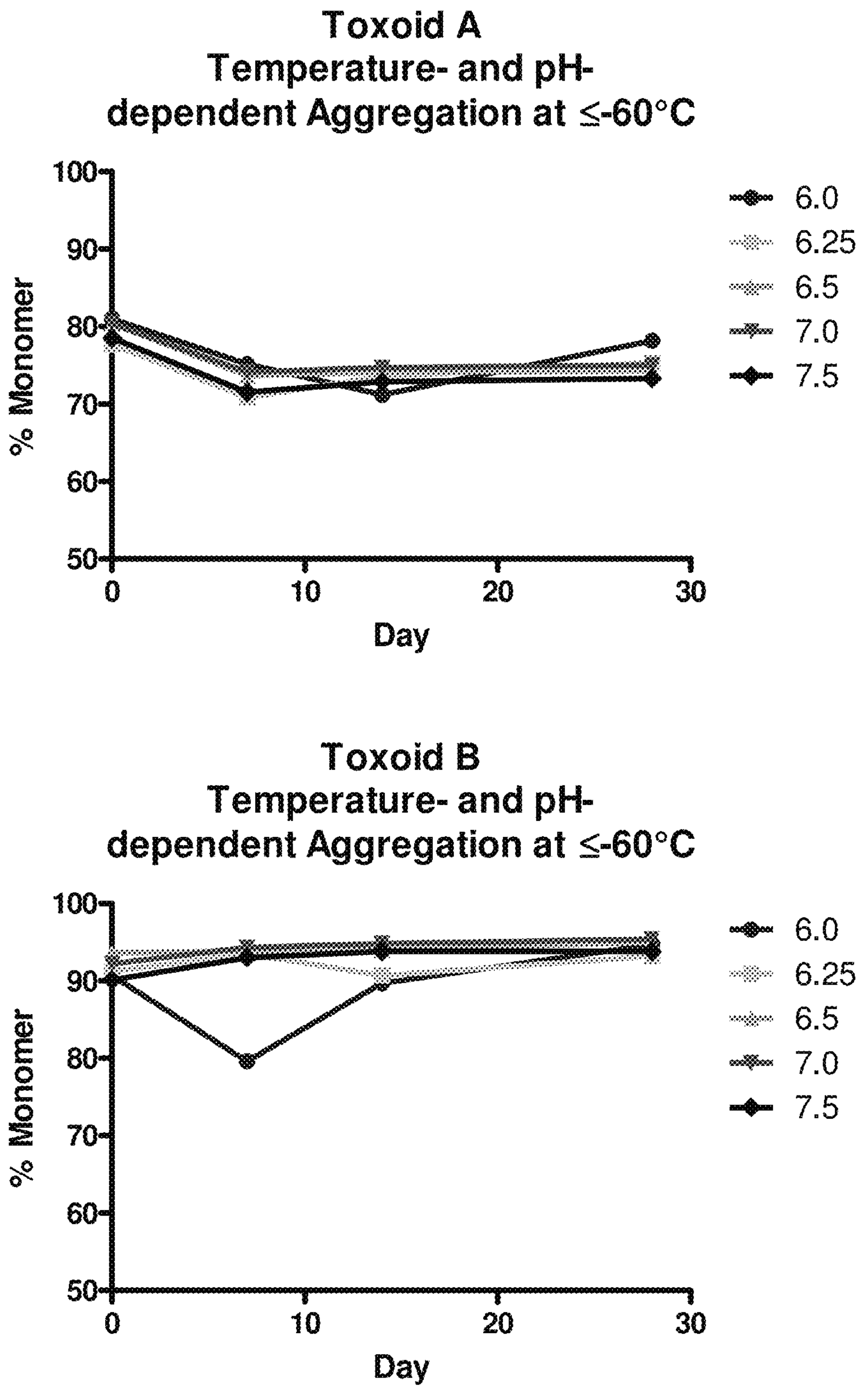
FIG. 13. Study of aggregation at different pH values over time at a fixed storage temperature.

When aggregation was assessed at different pH values over time at a fixed storage temperature (≤−60° C.) (FIG. 13), the results again indicated that the aggregation states were very stable at ultra-low temperature, with a suggestion that aggregation was promoted at lower pH levels (<pH 7.0). With these data in mind, the nominal pH for storage of the vaccine bulk was set to 7.5.

Ionic Strength

Determining the ionic strength that yields the maximum stability was also part of the formulation improvement effort. Studies were performed on liquid samples held at −65° C., 5° C., 25° C., and 37° C. for up to 28 days in 20 mM sodium citrate buffer, pH 7.25, with variable concentrations (0-300 mM) of sodium chloride. Also tested was replacing NaCl with 5% sucrose. The methods employed to establish the stability profile were SEC-HPLC, SDS-PAGE, and visual appearance.

No clear difference was discernable by SDS-PAGE or visible appearance.

Figure 14:
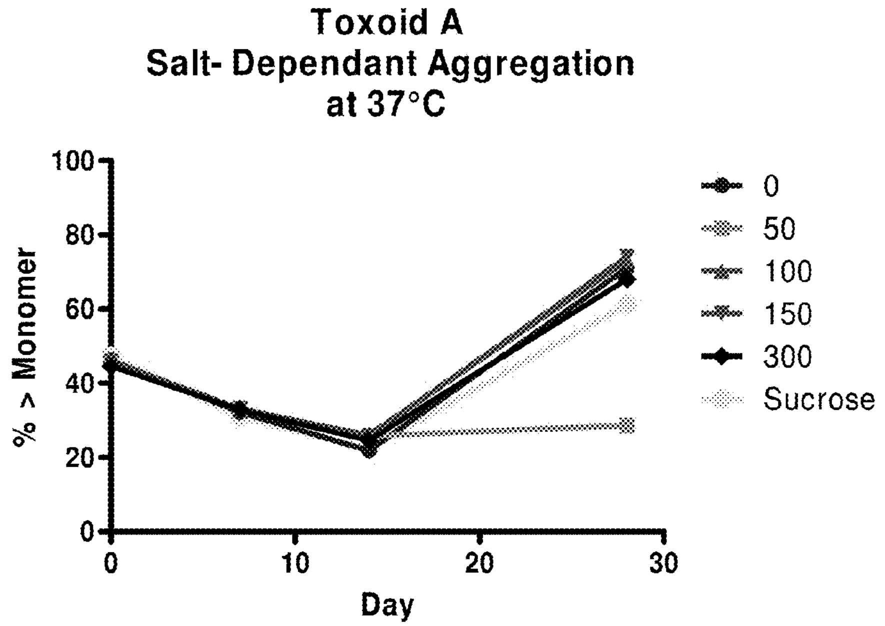
FIG. 14. Study of salt-dependent aggregation of toxoid A at 37° C. over time.
Figure 15:
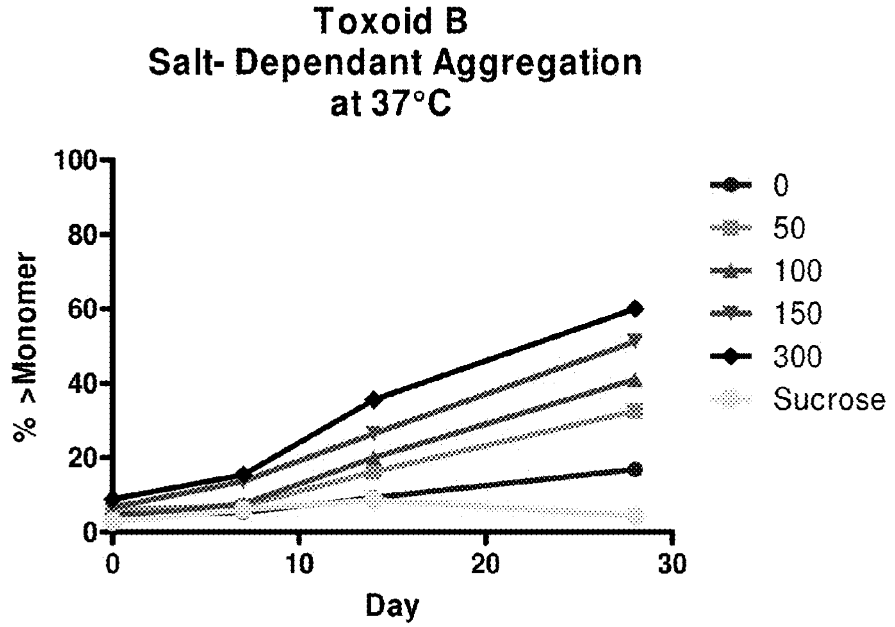
FIG. 15. Study of salt-dependent aggregation of toxoid B at 37° C. over time FIG. 16. Study of lyophilization parameters of vaccine formulations.

SEC-HPLC clearly showed aggregation of toxoid B at higher salt concentrations. Aggregation in toxoid A appeared to be time and temperature dependent with the only noticeable effect being seen at 50 mM NaCl. The data indicate that 0-50 mM sodium chloride or 5% sucrose should be added to achieve maximum stability of the toxoids (FIG. 14 and FIG. 15).

Buffer Change and Addition of Excipients

A preliminary study was performed to evaluate the buffer and excipient effect on the stability of the toxoids. Data derived from HPLC-SEC demonstrated that sodium citrate buffer with sorbitol as an excipient provided the greatest stability as determined by percent recovery of the toxoids over time, as shown in Table 8 and Table 9.

Evaluation of Lyophilized Preparations

In order to select a lyophilized formulation that would be stable for Phase II clinical trials, we employed a hamster immunogenicity assay, because it is the pre-clinical assay that demonstrates the greatest sensitivity to product changes that relate to clinical immunogenicity. Data from the preliminary studies led to an excipient screening study based on sodium citrate as a buffer and sorbitol as a stabilizing excipient. Sucrose was introduced as a stabilizing excipient as a replacement for sorbitol in the lyophilized formulations because of low Tg' and long lyophilization times observed in sorbitol formulations. A second lyophilization/excipient screening study was also performed using potassium phosphate buffer and trehalose based on data from a parallel study. From these studies and data from the previous experiments, three lead formulations, one liquid and two lyophilized emerged.

Lyophilized formulations were prepared and their stability assessed under real-time and accelerated conditions. Toxoids A and B were stored separately in order to more closely study their individual stability profiles. Appearance data and hamster immunogenicity data from one formulation (lyophilized, 20 mM citrate, 5% sucrose, 0.016% formaldehyde, pH 7.5) after storage at −65, 5 or 42° C. for hree months are presented below. Slight to no difference in appearance is observed between formulations at the study start and after storage at −65, 5, or 42° C. for 3 months (Table 10 and Table 11). In addition, the hamster immune response is not significantly different between the formulations stored at 5° and 42° C. for 7 months, or between the same formulations with and without formaldehyde. Storage at 42° C. is a highly stressed condition and, because no change is observed during storage, the results imply that the formulation will most likely be stable for considerably longer at lower temperatures. However, a statistically sound analysis of the data intended to estimate shelf life requires that some quantifiable change is seen such that a rate may be calculated. As no change is observed to date, no true rate can be calculated. In light of these data, we plan to use a lyophilized Drug Product formulation consisting of *C. difficile* toxoids A and B in 20 mM citrate, 5% sucrose, 0.016% formaldehyde, pH 7.5, stored at 2-8° C.

Figure 16:
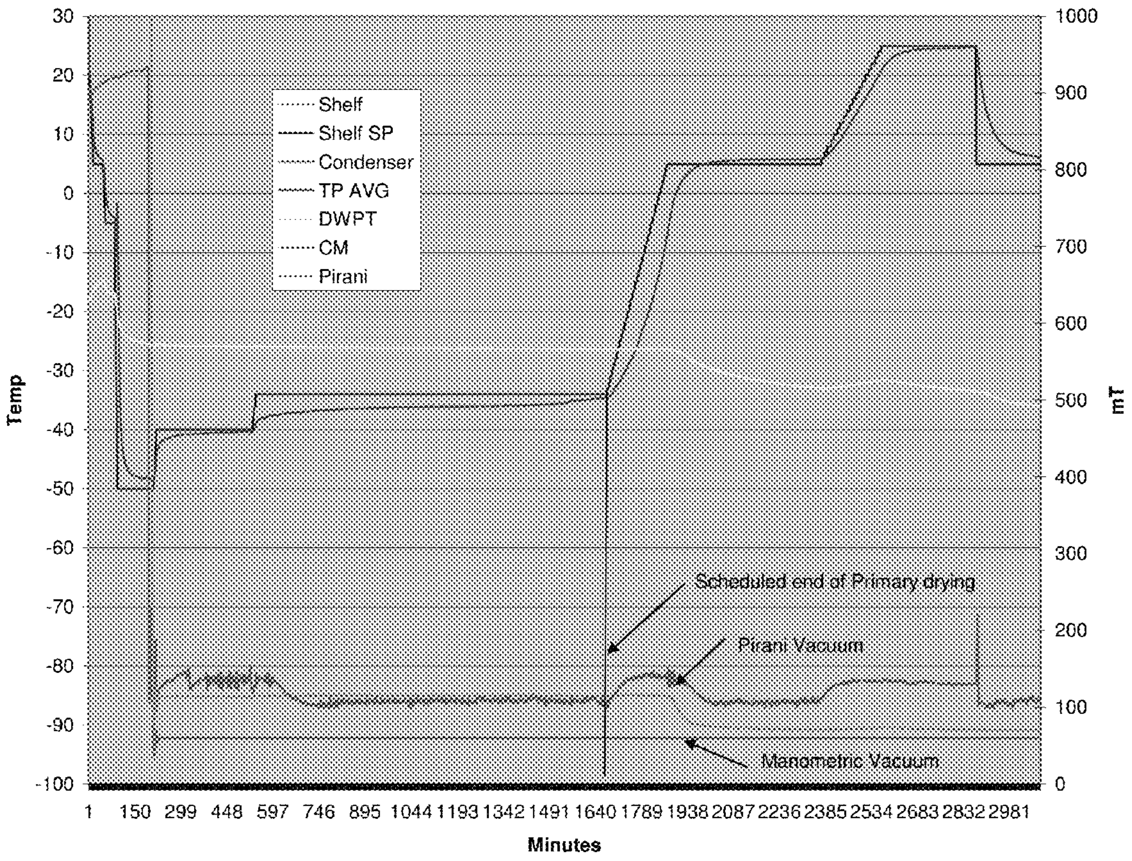

The formulations used in the stability studies detailed in this report were prepared using the lyophilization cycle summarized in Table 12. This cycle produced solid, white, elegant cakes but was on the very edge of completing primary drying as determined by the Pirani vacuum reading decreasing to equal the manometric vacuum reading (FIG. 16). The following critical changes were made to the lyophilization cycle to address this concern and create a more scaleable process:

1. The shelf temperature was reduced to −35° C. to ensure that the drug substance remained frozen during primary drying at a larger scale,
2. Primary drying was extended to 4000 minutes to ensure completion of primary drying at a larger scale, and
3. The vacuum was increased to 100 mT to expedite drying and allow for a more scaleable process.

The lyophilization cycle transferred to Althea Technologies, Inc. for the processing of GMP clinical lots is outlined in Table 13.

Summary of Physicochemical and Biological Properties

The key physicochemical and biological properties of the vaccine determined experimentally are summarized below.

Chemically, the vaccine is comprised of inactivated forms (toxoids) of *C. difficile* toxins A and B present at a 3:2 ratio, respectively. *C. difficile* toxins A and B are large proteins, 308 kDa and 270 kDa, respectively that are similar yet distinct in structure.

Physically, the vaccine is presented as a solution of ≥90% purity with no evidence of measurable aggregation.

Biochemically, the toxoids A and B of the vaccine are immunologically reactive to their respective toxin A or B-specific antibodies in a western blot analysis.

Biologically, the vaccine is immunogenic in hamsters, eliciting consistent and dose-dependent serum antibody responses. The vaccine toxoids A and B are devoid of cytotoxic activity. The toxoid A component of the vaccine retains some receptor-binding activity, like that observed for native toxin A.

The vaccine is presented as a lyophilized form in a buffer composed of 20 mM sodium citrate, pH 7.5, 5% sucrose, 0.016% formaldehyde. The product is stored at 2-8° C.

Lyophilization Screening Studies

In order to screen lyophilized formulations a hamster immunogenicity was employed for evaluation. Lyophilization took place in an FTS LyoStar II. Freezing was accomplished by reducing the shelf temperature low enough to force the product temperature below the Tg'. Primary drying commenced by pulling a vacuum and holding until the free water had been sublimed. The shelf temperature was then increased to begin secondary drying and held to further dry the product by driving off adsorbed water. Formulations were put on stability at temperature conditions of 5, 25, and 42° C.

TABLE 1

Effect of GRAS excipients on toxoid A aggregation. Compounds that delay/prevent aggregation have positive % of aggregation inhibition values; compounds that induce aggregation have negative % of aggregation inhibition values.

| Excipient, Concentration | % Inhibition of aggregation |
|---|---|
| Albumin 2.5% | 103* |
| α Cyclodextrin 2.5% | 101* |
| TWEEN 80 - 0.1% | 100* |
| Dietanolamine 0.3M | 100 |
| Sodium Citrate 0.1M | 100 |
| Sorbitol 10% | 100 |
| Histidine 0.3M | 100* |
| Sucrose 10% | 100 |
| Trehalose 10% | 100 |
| Guanidine 0.3M | 99 |
| Sorbitol 20% | 99 |
| Dextrose 20% | 99 |
| Dextrose 10% | 99 |
| Trehalose 20% | 99 |
| Sodium Citrate 0.2M | 99 |
| Glycerol 20% | 98 |
| TWEEN 80 - 0.01% | 98 |
| Albumin 1% | 98 |
| Lactose 20% | 98 |
| Mannitol 10% | 97 |
| Sucrose 20% | 97 |
| PLURONIC F-68 0.1% | 96 |
| 2-OH propyl β-CD 10% | 96 |
| 2-OH propyl β-CD 5% | 96 |
| Dextran T40 0.08 mg/ml | 95 |
| BRIJ 35 0.1% | 95 |
| Dextran T40 0.03 mg/ml | 93 |
| Lactose 10% | 92 |
| Lysine 0.3M | 89* |
| Glycerol 10% | 88 |
| 2-OH propyl γ-CD 10% | 81 |
| TWEEN 20 - 0.05% | 73 |
| TWEEN 80 - 0.05% | 67 |
| Aspartic Acid 0.15M | 65 |
| TWEEN 20 - 0.1% | 64 |
| PLURONIC F - 68 0.05% | 50 |
| TWEEN 20 - 0.01% | 37 |
| Dextran Sulfate 0.04 mg/ml | 30 |
| BRIJ 35 0.05% | 26 |
| Dextran Sulfate 0.004 mg/ml | 16 |
| 2-OH propyl γ-CD 5% | 10 |
| Albumin 5% | 9 |
| BRIJ 35 0.01% | −2 |
| Calcium Chloride 0.015M | −7 |
| PLURONIC F-68 0.01% | −14 |
| Gelatin 5% | −46 |
| Malic Acid 0.15M | −52 |
| Lactic Acid 0.15M | −72 |
| Gelatin 2.5% | −74 |
| Glutamic Acid 0.15M | −77 |
| Dextran T40 0.003 mg/ml | −87 |
| Glycine 0.3M | −88 |
| Dextran Sulfate 0.1 mg/ml | −88 |
| Ascorbic Acid 0.15M | −99 |
| Proline 0.3M | −112 |
| Arginine 0.3M | −265 |
| Arg/Glu 50 mM each | −426 |
| Arg/Glu 25 mM each | −463 |

Uncertainties are on the order of ±1%.
*High initial OD 350 nm.

TABLE 2

Effect of GRAS excipients on toxoid B aggregation. Compounds that delay/prevent aggregation have positive % of aggregation inhibition values; compounds that induce aggregation have negative % of aggregation inhibition values.

| Excipient, Concentration | % Inhibition of aggregation |
|---|---|
| α Cyclodextrin 2.5% | 100 |
| Histidine 0.3M | 100* |
| TWEEN 80 - 0.1% | 100 |
| TWEEN 80 - 0.05% | 100 |
| Albumin 1% | 99 |
| Dextrose 20% | 99 |
| Albumin 5% | 98 |
| Sodium Citrate 0.2M | 98* |
| Trehalose 20% | 98 |
| Sodium Citrate 0.1M | 97 |
| Sorbitol 20% | 97 |
| Sucrose 20% | 96 |
| Dietanolamine 0.3M | 96 |
| Dextrose 10% | 95 |
| Sorbitol 10% | 92 |
| Albumin 2.5% | 87 |
| 2-OH propyl β-CD 5% | 79 |
| 2-OH propyl β-CD 10% | 78 |
| Mannitol 10% | 76 |
| Sucrose 10% | 71 |
| Glycerol 20% | 71 |
| Trehalose 10% | 69 |
| PLURONIC F-68 0.1% | 68 |
| BRIJ 35 0.1% | 63 |
| Lactose 20% | 52 |
| Malic Acid 0.15M | 44 |
| TWEEN 80 - 0.01% | 40 |
| Lactose 10% | 39 |
| Lysine 0.3M | 37 |
| Dextran T40 0.03 mg/ml | 35 |
| Dextran T40 0.08 mg/ml | 25 |
| 2-OH propyl γ-CD 10% | 12 |
| BRIJ 35 0.05% | 10 |
| PLURONIC F-68 0.05% | 6 |
| Glycerol 10% | 4 |
| Dextran Sulfate 0.04 mg/ml | 3 |
| Dextran Sulfate 0.004 mg/ml | 2 |
| TWEEN 20 - 0.05% | 0 |
| 2-OH propyl γ-CD 5% | −5 |
| TWEEN 20 - 0.01% | −5 |
| PLURONIC F-68 0.01% | −8 |
| TWEEN 20 - 0.1% | −13 |
| BRIJ 35 0.01% | −25 |
| Glycine 0.3M | −26 |
| Gelatin 2.5% | −36 |
| Dextran Sulfate 0.1 mg/ml | −38 |
| Arg/Glu 50 mM each | −39 |
| Glutamic Acid 0.15M | −41 |
| Arg/Glu 25 mM each | −42 |
| Aspartic Acid 0.15M | −50 |
| Gelatin 5% | −56 |
| Proline 0.3M | −57 |
| Dextran T40 0.003 mg/ml | −59 |
| Lactic Acid 0.15M | −80 |
| Guanidine 0.3M | −96 |
| Calcium Chloride 0.015M | −141 |
| Ascorbic Acid 0.15M | −223 |
| Arginine 0.3M | −280 |

Uncertainties are on the order of ±1%.
*High initial OD 350 nm.

TABLE 3

Effect of solutes (detergents) on the thermal stability of toxoid A and B. The thermal stability (Tm) was monitored by DSC. The Tm is the temperature corresponding to the maximum peak position of the thermal transition.

| Protein | Tm (° C.) |
|---|---|
| Toxoid A | 59.8 ± 0.0 |
| Toxoid A + 0.05% TWEEN 80 | 59.1 ± 0.4 |
| Toxoid A + 0.1% PLURONIC F68 | 59.1 ± 0.4 |
| Toxoid B | 55.8 ± 0.0 |
| Toxoid B + 0.05% TWEEN 80 | 56.1 ± 0.3 |
| Toxoid B + 0.1% PLURONIC F68 | 58.0 ± 0.3 |

TABLE 4

Effect of excipients on the toxoid A midpoint of the thermal transition temperature (Tm). The thermal transition was monitored by the CD signal at 208 nm as a function of temperature. Each measurement was conducted in duplicate and has ~0.5° C. of uncertainty.

| Toxoid A in presence of excipient(s) | Tm | Tm difference |
|---|---|---|
| Toxoid A | 59.8 | 0.0 |
| 20% trehalose | 59.4 | −0.5 |
| 20% sucrose | 63.1 | 3.3 |
| 20% glycerol | 62.4 | 2.6 |
| 0.1% PLURONIC F68 | 61.1 | 1.3 |
| 10% sorbitol | 62.4 | 2.6 |
| 10% dextrose | 62.4 | 2.6 |
| 0.05% TWEEN 80 | 59.9 | 0.0 |
| 5% sorbitol + 0.05% TWEEN 80 | 60.4 | 0.6 |
| 10% sorbitol + 0.05% TWEEN 80 | 62.3 | 2.5 |
| 15% sorbitol + 0.05% TWEEN 80 | 62.4 | 2.6 |
| 5% dextrose + 0.05% TWEEN 80 | 60.2 | 0.4 |
| 10% dextrose + 0.05% TWEEN 80 | 62.3 | 2.5 |
| 15% dextrose + 0.05% TWEEN 80 | 62.5 | 2.7 |
| 2.5% sorbitol + 2.5% dextrose + 0.05% TWEEN 80 | 60.2 | 0.4 |
| 5% sorbitol + 5% dextrose + 0.05% TWEEN 80 | 61.3 | 1.5 |
| 10% sorbitol + 10% dextrose + 0.05% TWEEN 80 | 63.5 | 3.7 |
| 0.1% TWEEN 80 | 59.0 | −0.8 |
| 10% sorbitol + 0.1% TWEEN 80 | 60.6 | 0.7 |
| 10% dextrose + 0.1% TWEEN 80 | 61.5 | 1.7 |
| 2.5% sorbitol + 2.5% dextrose + 0.1% TWEEN 80 | 60.0 | 0.2 |
| 5% sorbitol + 5% dextrose + 0.1% TWEEN 80 | 60.5 | 0.7 |
| 10% sorbitol + 10% dextrose + 0.1% TWEEN 80 | 62.1 | 2.3 |
| 2.5% sorbitol + 2.5% dextrose | 60.8 | 0.9 |
| 5% sorbitol + 5% dextrose | 61.7 | 1.8 |
| 10% sorbitol + 10% dextrose | 63.9 | 4.0 |
| 15% sorbitol + 15% dextrose | 64.6 | 4.8 |
| 20% sorbitol + 20% dextrose | 66.6 | 6.7 |
| 20% sorbitol + 10% dextrose | 64.9 | 5.1 |
| 10% sorbitol + 20% dextrose | 50.1 | −9.7 |

TABLE 5

Effect of excipients on the toxoid B midpoint of thermal transition temperature (Tm). The thermal transition was monitored by the CD signal at 208 nm as a function of temperature. Each measurement was conducted in duplicate and has ~0.5° C. of uncertainty.

| Toxoid B in presence of excipient(s) | Tm | Tm difference |
|---|---|---|
| Toxoid B | 55.8 | 0.0 |
| 20% trehalose | 60.3 | 4.5 |
| 20% sucrose | — | — |
| 20% glycerol | 58.6 | 2.8 |
| 0.1% PLURONIC F68 | 56.2 | 0.4 |
| 10% sorbitol | 56.6 | 0.8 |
| 10% dextrose | 57.3 | 1.6 |
| 0.05% TWEEN 80 | 55.1 | −0.7 |

TABLE 5-continued

Effect of excipients on the toxoid B midpoint of thermal transition temperature (Tm). The thermal transition was monitored by the CD signal at 208 nm as a function of temperature. Each measurement was conducted in duplicate and has ~0.5° C. of uncertainty.

| Toxoid B in presence of excipient(s) | Tm | Tm difference |
|---|---|---|
| 5% sorbitol + 0.05% TWEEN 80 | 56.7 | 0.9 |
| 10% sorbitol + 0.05% TWEEN 80 | 63.2 | 7.4 |
| 15% sorbitol + 0.05% TWEEN 80 | 64.0 | 8.2 |
| 5% dextrose + 0.05% TWEEN 80 | 59.1 | 3.3 |
| 10% dextrose + 0.05% TWEEN 80 | 70.8 | 15.0 |
| 2.5% sorbitol + 2.5% dextrose + 0.05% TWEEN 80 | 56.7 | 0.9 |
| 5% sorbitol + 5% dextrose + 0.05% TWEEN 80 | 63.5 | 7.7 |
| 10% sorbitol + 10% dextrose + 0.05% TWEEN 80 | 69.1 | 13.3 |
| 0.1% TWEEN 80 | 53.6 | −2.2 |
| 10% sorbitol + 0.1% TWEEN 80 | 58.5 | 2.7 |
| 10% dextrose + 0.1% TWEEN 80 | 62.6 | 6.9 |
| 2.5% sorbitol + 2.5% dextrose + 0.1% TWEEN 80 | 60.0 | 4.2 |
| 5% sorbitol + 5% dextrose + 0.1% TWEEN 80 | 56.5 | 0.8 |
| 10% sorbitol + 10% dextrose + 0.1% TWEEN 80 | 60.8 | 5.1 |
| 5% sorbitol + 5% dextrose | 56.5 | 0.7 |
| 10% sorbitol + 10% dextrose | 65.3 | 9.6 |
| 15% sorbitol + 15% dextrose | 60.1 | 4.4 |
| 20% sorbitol + 20% dextrose | 63.1 | 7.3 |
| 20% sorbitol + 10% dextrose | 38.0 | −17.8 |
| 10% sorbitol + 20% dextrose | 61.2 | 5.5 |

TABLE 6

Thermal stability of toxoid A bound to Alhydrogel ® (aluminum hydroxide adjuvant) in the presence and absence of excipient(s) (unless specified otherwise). The thermal stability (Tm) was monitored by DSC, with the Tm indicating the temperature corresponding to the peak position of the thermal transition. The percent of toxoid bound to adjuvant was measured in each condition with an uncertainty of 1%. Each condition was studied in duplicate.

| Toxoid A bound to ALHYDROGEL ® (aluminum hydroxide adjuvant) in the presence of solutes | % of bound protein | Tm | Tm difference |
|---|---|---|---|
| Toxoid A not bound | — | 58.8 ± 0.4 | 0.1 |
| Toxoid A | 96 | 58.7 ± 0.3 | — |
| 10% sorbitol | 81 | 52.4 ± 1.5 | −6.2 |
| 10% dextrose | 86 | 60.6 ± 0.5 | 2.0 |
| 0.05% TWEEN 80 | 93 | 58.7 ± 0.1 | 0.0 |

TABLE 6-continued

Thermal stability of toxoid A bound to Alhydrogel ® (aluminum hydroxide adjuvant) in the presence and absence of excipient(s) (unless specified otherwise). The thermal stability (Tm) was monitored by DSC, with the Tm indicating the temperature corresponding to the peak position of the thermal transition. The percent of toxoid bound to adjuvant was measured in each condition with an uncertainty of 1%. Each condition was studied in duplicate.

| Toxoid A bound to ALHYDROGEL ® (aluminum hydroxide adjuvant) in the presence of solutes | % of bound protein | Tm | Tm difference |
|---|---|---|---|
| 10% sorbitol + 10% dextrose | 77 | 62.9 ± 0.0 | 4.2 |
| 10% sorbitol + 10% dextrose + 0.05% TWEEN 80 | 81 | 63.1 ± 1.2 | 4.2 |
| 10% sorbitol + 10% dextrose + 0.1% TWEEN 80 | 74 | 62.0 ± 1.3 | 3.3 |
| 10% sorbitol + 0.05% TWEEN 80 | 86 | 59.3 ± 0.8 | 0.7 |
| 10% dextrose + 0.05% TWEEN 80 | 85 | 59.5 ± 1.1 | 0.8 |

TABLE 7

The thermal stability of toxoid B bound to Alhydrogel ® (aluminum hydroxide adjuvant) in the presence and absence of solute(s) (unless specified otherwise). The thermal stability (Tm) was monitored by DSC. The Tm indicates the temperature corresponding to the peak position of the thermal transition. The percent of protein bound to adjuvant was measured under each condition with an uncertainty of 1%. Each condition was studied in duplicate.

| Toxoid B bound to ALHYDROGEL ® (aluminum hydroxide adjuvant) in the presence of solute(s) | % of bound protein | Tm | Tm difference |
|---|---|---|---|
| Toxoid B not bound | — | 56.2 ± 0.4 | 1.4 |
| Toxoid B | 99 | 54.8 ± 0.5 | — |
| 10% sorbitol | 92 | 52.5 ± 1.4 | −2.2 |
| 10% dextrose | 96 | 57.9 ± 0.2 | 3.1 |
| 0.05% TWEEN 80 | 96 | 58.2 ± 0.6 | 3.4 |
| 10% sorbitol + 10% dextrose | 95 | 54.2 ± 0.9 | −0.5 |
| 10% sorbitol + 10% dextrose + 0.05% TWEEN 80 | 99 | 58.0 ± 2.8 | 3.3 |
| 10% sorbitol + 10% dextrose + 0.1% TWEEN 80 | 77 | 58.7 ± 1.0 | 3.9 |
| 10% sorbitol + 0.05% TWEEN 80 | 96 | 58.5 ± 1.0 | 3.8 |
| 10% dextrose + 0.05% TWEEN 80 | 92 | 55.8 ± 2.5 | 1.1 |

TABLE 8

Toxoid A
2 Month Stability
% Toxoid Recovery

| Temperature (° C.) | 20 mM Sodium Phosphate, 50 mM NaCL pH 7.5 TXD A | 20 mM Sodium Phosphate, 4% Sorbitol pH 7.5 TXD A | 20 mM Sodium Phosphate, 4% Trehalose pH 7.5 TXD A | 20 mM Sodium Citrate, 50 mM NaCL pH 7.5 TXD A | 20 mM Sodium Citrate, 4% Sorbitol pH 7.5 TXD A | 20 mM Sodium Citrate, 4% Trehalose pH 7.5 TXD A |
|---|---|---|---|---|---|---|
| −65 | 95.0 | 91.2 | 90.2 | 100.0 | 54.6 | 90.1 |
| 5 | 88.3 | 91.7 | 86.4 | 99.2 | 96.8 | 88.3 |
| 25 | 83.5 | 88.0 | 62.9 | 91.8 | 93.5 | 64.0 |

| Temperature (° C.) | 20 mM Histidine, 50 mM NaCl pH 7.5 TXD A | 20 mM Histidine, 4% Sorbitol pH 7.5 TXD A | 20 mM Hepes, 50 mM NaCl pH 7.5 TXD A | 20 mM Hepes, 4% Sorbitol pH 7.5 TXD A | 75 mM Histidine, 0.05% PS20 pH 7.5 TXD A | 75 Mm Diethanolamine, 0.05% PS20 pH 7.5 TXD A |
|---|---|---|---|---|---|---|
| −65 | 69.2 | 75.2 | 89.9 | 91.0 | 80.8 | 52.6 |
| 5 | 64.3 | 72.9 | 88.0 | 89.0 | 79.5 | 37.7 |
| 25 | 63.0 | 69.0 | 78.9 | 88.2 | 55.3 | 23.1 |

TABLE 9

Toxoid B
2 Month Stability
% Toxoid Recovery

| Temperature (° C.) | 20 mM Sodium Phosphate, 50 mM NaCL pH 7.5 TXD B | 20 mM Sodium Phosphate, 4% Sorbitol pH 7.5 TXD B | 20 mM Sodium Phosphate, 4% Trehalose pH 7.5 TXD B | 20 mM Sodium Citrate, 50 mM NaCL pH 7.5 TXD B | 20 mM Sodium Citrate, 4% Sorbitol pH 7.5 TXD B | 20 mM Sodium Citrate, 4% Trehalose pH 7.5 TXD B |
|---|---|---|---|---|---|---|
| −65 | 76.72% | 78.52% | 65.97% | 100.00% | 90.11% | 77.84% |
| 5 | 74.52% | 78.82% | 36.44% | 84.36% | 86.73% | 47.83% |
| 25 | 71.88% | 78.93% | 1.83% | 84.31% | 86.65% | 4.07% |

| Temperature (° C.) | 20 mM Histidine, 50 mM NaCl pH 7.5 TXD B | 20 mM Histidine, 4% Sorbitol pH 7.5 TXD B | 20 mM Hepes, 50 mM NaCl pH 7.5 TXD B | 20 mM Hepes, 4% Sorbitol pH 7.5 TXD B | 75 mM Histidine, 0.05% PS20 pH 7.5 TXD B | 75 mM Diethanolamine, 0.05% PS20 pH 7.5 TXD B |
|---|---|---|---|---|---|---|
| −65 | 59.70% | 66.97% | 75.73% | 82.54% | 62.44% | 57.79% |
| 5 | 60.20% | 67.34% | 77.68% | 80.69% | 34.20% | 26.13% |
| 25 | 55.15% | 60.48% | 73.23% | 75.14% | 0.00% | 1.15% |

TABLE 10

Appearance of a Lyophilized Formulation following storage at different temperatures

| Molecule | Attribute | Initiation | Appearance After 3 Months At: −65° C. | 5° C. | 42° C. |
|---|---|---|---|---|---|
| Toxoid A | Cake Appearance | white, minimal shrinkage | white, minimal shrinkage | white, minimal shrinkage | white, minimal shrinkage |
| | Reconstitution Time | <10 sec | <1 min | <1 min | <1 min |
| | Liquid Appearance | Clear Colorless No particulates | Clear Colorless No particulates | Clear Colorless No particulates | Clear Colorless No particulates |
| Toxoid B | Cake Appearance | white, minimal shrinkage | white, slight collapse at bottom | white, slight collapse at bottom | white, minimal shrinkage |
| | Reconstitution Time | <10 sec | <1 min | <1 min | <1 min |
| | Liquid Appearance | Clear Colorless No particulates | Clear Colorless No particulates | Clear Colorless No particulates | Clear Colorless No particulates |

TABLE 11

Immunogenicity of a Lyophilized Formulation following storage at different temperatures (serum anti-toxin A and B IgG titers in hamsters).

| Molecule | Formulation Description: A:B Ratio = 3:2, Total protein = 0.4 mg/mL | 20 mM Citrate, 5% Sucrose, pH 7.5 Lyophilized<br>Storage Temp<br>5° C. | 25° C. | 42° C. | 20 mM Citrate, 5% Sucrose, 0.016% $H_2CO$, pH 7.5 Lyophilized<br>5° C. | 25° C. | 42° C. |
|---|---|---|---|---|---|---|---|
| | | $Log_{10}$ Median | | | $Log_{10}$ Median | | |
| Toxoid A | 1 Month | 5.34 | — | 5.26 | — | — | — |
| | 3 Months | 5.57 | — | 5.56 | — | — | 5.42 |
| | 5 Months | 5.33 | 5.23 | — | — | 5.30 | — |
| | 7 Months | — | 5.49 | 5.41 | 5.47 | 5.45 | — |
| | Log change | −0.01 | 0.26 | 0.15 | — | 0.15 | — |
| Toxoid B | 1 Month | 5.49 | — | 5.62 | — | — | — |
| | 3 Months | 5.54 | — | 5.42 | — | — | 5.23 |

TABLE 11-continued

Immunogenicity of a Lyophilized Formulation following storage at different temperatures (serum anti-toxin A and B IgG titers in hamsters).

| Molecule | Formulation Description: A:B Ratio = 3:2, Total protein = 0.4 mg/mL | 20 mM Citrate, 5% Sucrose, pH 7.5 Lyophilized 5° C. | 25° C. | 42° C. | 20 mM Citrate, 5% Sucrose, 0.016% $H_2CO$, pH 7.5 Lyophilized 5° C. | 25° C. | 42° C. |
|---|---|---|---|---|---|---|---|
| | | Storage Temp Log10 Median | | | Log10 Median | | |
| | 5 Months | 5.62 | 5.34 | — | — | 5.49 | — |
| | 7 Months | — | 5.49 | 5.62 | 5.70 | 5.78 | — |
| | Log change | 0.13 | 0.15 | 0 | — | 0.29 | — |

$H_2CO$ = formaldehyde

TABLE 12

| Freeze |
|---|
| Ramp shelves at 1° C./minute to 5° C. Hold for 30 minutes.<br>Ramp shelves at 1° C./minute to −5° C. Hold for 30 minutes.<br>Ramp shelves at 5° C./minute to −50° C. Hold for 90 minutes.<br>Turn on vacuum with a set point of 60 mT. |
| **Primary Drying** |
| Ramp shelves at 1° C./minute to −40° C. Hold for 300 minutes.<br>Vacuum equals 60 mT.<br>Ramp shelves at 0.5° C./minute to −34° C. Hold for 1100 minutes.<br>Vacuum equals 60 mT |
| **Secondary Drying** |
| Ramp shelves at 0.2° C./minute to 5° C. Hold for 480 minutes.<br>Vacuum equals 60 mT.*<br>Ramp shelves at 0.1° C./minute to 25° C. Hold for 300 minutes.<br>Vacuum equals 60 mT. |
| **Hold Step** |
| Ramp shelves at 0.5° C./minute to 0° C. Hold for 9999 minutes.<br>Vacuum equals 100 mT. |
| **Backfill** |
| Backfill to 600,000 mT with dry purified $N_2$. |

TABLE 13

| Freeze |
|---|
| Ramp shelves at 1° C./minute to 5° C. Hold for 30 minutes.<br>Ramp shelves at 0.5° C./minute to −45° C. Hold for 120 minutes.<br>Turn on vacuum with a set point of 100 mT |
| **Primary Drying** |
| Ramp shelves at 0.2° C./minute to −35° C. Hold for 4000 minutes.<br>Vacuum set point at 100 mT |
| **Secondary Drying** |
| Ramp shelves at 0.2° C./minute to 5° C. Hold for 480 minutes. Vacuum set point at 100 mT<br>Ramp shelves at 0.2° C./minute to 25° C. Hold for 300 minutes.<br>Vacuum set point at 100 mT |
| **Hold Step** |
| Ramp shelves at 0.5° C./minute to 0° C. Hold for 9999 minutes. Vacuum set point at 100 mT |
| **Backfill** |
| Backfill to 600,000 mT with dry purified $N_2$ |

The contents of all references cited above are incorporated herein by reference. Use of singular forms herein, such as “a” and “the,” does not exclude indication of the corresponding plural form, unless the context indicates to the contrary. Thus, for example, if a claim indicates the use of “a” toxin, toxoid, or excipient, it can also be interpreted as covering use of more than one toxin, toxoid, or excipient, unless otherwise indicated. Other embodiments are within the following claims.

What is claimed is:

1. A method for inducing an immune response to *Clostridium difficile* in a subject, the method comprising administering to the subject a composition comprising:

(a) a toxoid of *Clostridium difficile* toxin A and/or B; and (b) a sugar or sugar alcohol selected from sucrose, sorbitol, dextrose, and trehalose at a concentration of 1-30%.

2. The method of claim 1, wherein the sugar or sugar alcohol is selected from sucrose, sorbitol, and trehalose at a concentration of 1-30%.

3. The method of claim 1, wherein the composition comprises a toxoid of *Clostridium difficile* toxins A and B.

4. The method of claim 3, wherein the *C. difficile* toxoids A and B are present in the composition in a ratio of 5:1 (A:B) to 1:5 (A:B), or are present in the composition in a ratio of 3:1 to 3:2, or 1:1 (A:B).

5. The method of claim 1, wherein the sugar or sugar alcohol is at a concentration of 5-10%.

6. The method of claim 1, wherein the composition further comprises a buffer selected from a citrate, phosphate, glycine, histidine, carbonate, bicarbonate, and 4-(2-hydroxyethyl)-1-piperazineethanesulfonic add (HEPES) buffer at a concentration of 5-100 mM.

7. The method of claim 6, wherein the buffer is a citrate buffer or a phosphate buffer at a concentration of 5-100 mM.

8. The method of claim 6, wherein the buffer is sodium citrate or potassium citrate.

9. The method of claim 6, wherein the buffer is sodium phosphate or potassium phosphate.

10. The method of claim 6, wherein the buffer is at a concentration of 10-30 mM.

11. The method of claim 1, wherein the buffer is at a concentration of 10-30 mM.

12. The method of claim 1, wherein the composition further comprises formaldehyde.

13. The method of claim 1, wherein the pH of the composition is 5.5-8.0.

14. The method of claim 13, wherein the pH of the composition is 6.5-8.0.

15. The method of claim 1, wherein the composition is a pharmaceutical composition.

16. The method of claim 1, wherein the composition further comprises an adjuvant.

17. The method of claim 16, wherein the adjuvant comprises an aluminum compound.

18. The method of claim 17, wherein the aluminum compound is an aluminum hydroxide compound.

19. The method of claim 1, wherein the composition is in liquid form.

20. The method of claim 19, further comprising reconstituting a dried composition to form said composition in liquid form.

21. The method of claim 6, wherein the buffer and/or the sugar or sugar alcohol of the composition increases thermal stability of the toxoid and/or reduces aggregation of the toxoid, relative to a composition lacking the buffer and/or sugar or sugar alcohol.

22. A method for inducing an immune response to *Clostridium difficile* in a subject, the method comprising administering to the subject a composition comprising:

(a) a toxoid of *Clostridium difficile* toxin A and/or B;

(b) sodium or potassium citrate (5-100 mM);

(c) sucrose (2-20%); and (d) formaldehyde;

wherein the pH of the composition is 5.5-8.5.

23. The method of claim 22, wherein the composition comprises sodium or potassium citrate in the amount of 10-30 mM, sucrose in the amount of 2-10%, and formaldehyde in the amount of 0.01-0.018%, wherein the pH of the composition is 6.5-8.0.

24. The method of claim 22, wherein the composition comprises a toxoid of *Clostridium difficile* toxin A and toxin B.

25. The method of claim 22, wherein the composition is in liquid form.

26. A method for inducing an immune response to *Clostridium difficile* in a subject, the method comprising administering to the subject a composition comprising:

(a) a toxoid of *Clostridium difficile* toxin A and/or B;

(b) sodium or potassium phosphate (5-100 mM);

(c) sucrose (2-20%); and (d) formaldehyde;

wherein the pH of the composition is 5.5-8.5.

27. The method of claim 26, wherein the composition comprises sodium or potassium phosphate in the amount of 10-30 mM, sucrose in the amount of 2-10%, and formaldehyde in the amount of 0.01-0.018%, wherein the pH of the composition is 6.5-8.0.

28. The method of claim 26, wherein the composition comprises a toxoid of *Clostridium difficile* toxin A and toxin B.

29. The method of claim 26, wherein the composition is in liquid form.

30. The method of claim 29, further comprising reconstituting a dried composition to form said composition in liquid form.

31. The method of claim 1, wherein the patient does not have, but is at risk of developing, *C. difficile* disease.

32. The method of claim 1, wherein the patient has *C. difficile* disease.

* * * * *

UNITED STATES PATENT AND TRADEMARK OFFICE
CERTIFICATE OF CORRECTION

PATENT NO. : 9,687,541 B2
APPLICATION NO. : 15/083428
DATED : June 27, 2017
INVENTOR(S) : C. Russell Middaugh et al.

Page 1 of 1

It is certified that error appears in the above-identified patent and that said Letters Patent is hereby corrected as shown below:

On the Title Page

Item (73), in Assignee, replace "Sanofi Pasteur Biologies, LLC," with --Sanofi Pasteur Biologics, LLC,--.

In the Specification

Column 15, Line 7, replace "hree" with --three--.

In the Claims

Column 24, Line 56, replace "The method of claim 1, wherein" with --The method of claim 7, wherein--.

Signed and Sealed this
Thirtieth Day of July, 2019

Andrei Iancu
*Director of the United States Patent and Trademark Office*